(12) United States Patent
Smith

(10) Patent No.: US 9,977,035 B2
(45) Date of Patent: May 22, 2018

(54) ASSAY FOR NITRATED AND TOTAL HEMOPEXIN IN FLUID SAMPLES

(71) Applicant: Ann Smith, Kansas City, MO (US)

(72) Inventor: Ann Smith, Kansas City, MO (US)

(*) Notice: Subject to any disclaimer, the term of this patent is extended or adjusted under 35 U.S.C. 154(b) by 217 days.

(21) Appl. No.: 14/961,144

(22) Filed: Dec. 7, 2015

(65) Prior Publication Data

US 2016/0195545 A1    Jul. 7, 2016

Related U.S. Application Data

(60) Provisional application No. 62/088,920, filed on Dec. 8, 2014.

(51) Int. Cl.
*G01N 33/53* (2006.01)
*G01N 33/68* (2006.01)

(52) U.S. Cl.
CPC ..... *G01N 33/6893* (2013.01); *G01N 33/5308* (2013.01); *G01N 2333/47* (2013.01); *G01N 2800/22* (2013.01); *G01N 2800/26* (2013.01); *G01N 2800/2871* (2013.01)

(58) Field of Classification Search
None
See application file for complete search history.

(56) References Cited

U.S. PATENT DOCUMENTS

2007/0218501 A1* 9/2007 Fogelman ............ G01N 33/721
435/7.1

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*

* cited by examiner

*Primary Examiner* — Gary Counts
(74) *Attorney, Agent, or Firm* — John C. McMahon

(57) ABSTRACT

A method of detecting and measuring the level of total hemopexin and nitrated hemopexin in a sample of a patient in need thereof. The method uses an ELISA for total and nitrated hemopexin.

9 Claims, 15 Drawing Sheets

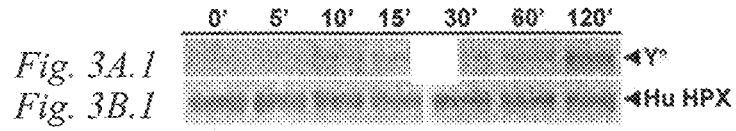
Fig. 3A.1
Fig. 3B.1
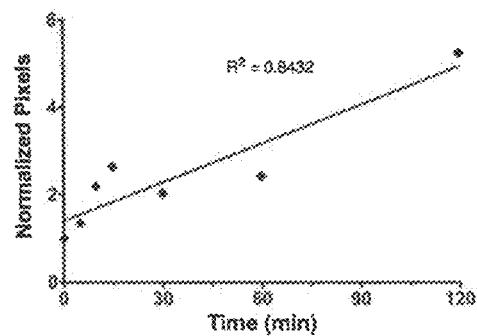
Fig. 3A.2
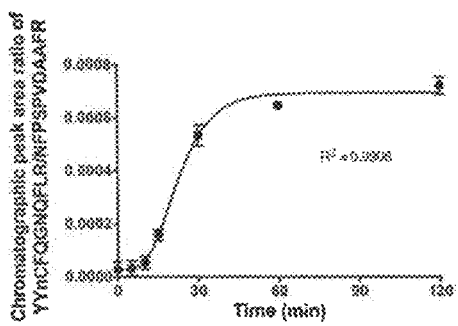
Fig. 3B.2
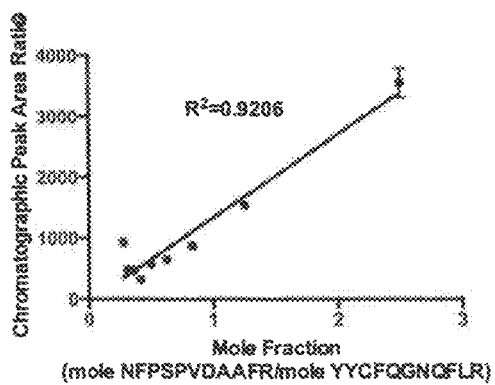
Fig. 3D

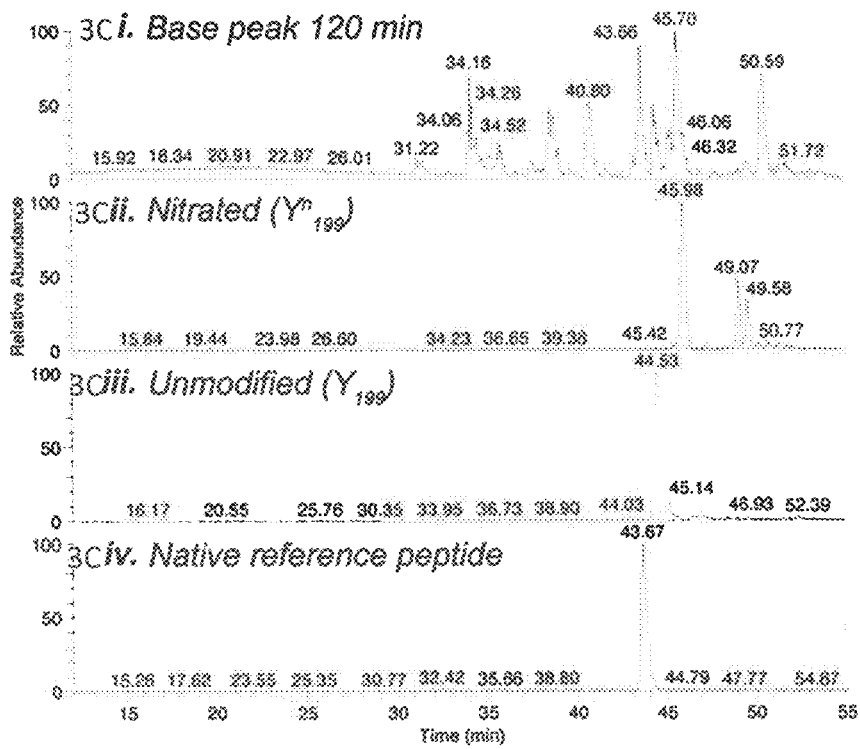

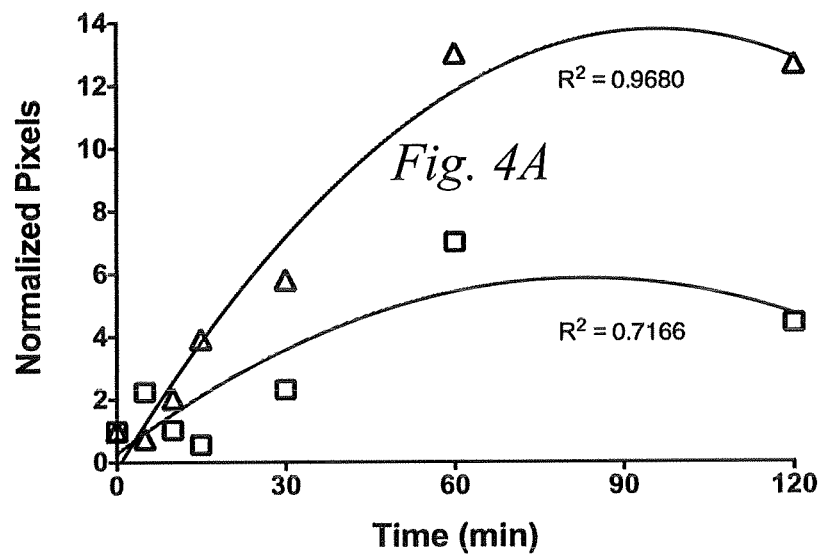
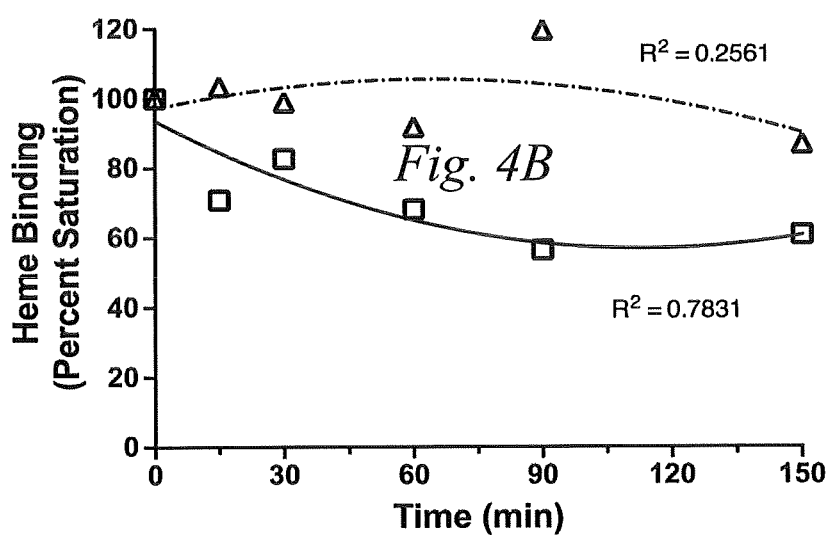

Fig. 8

| # | b | b$^{++}$ | b* | b*$^{++}$ | Seq. | y | y$^{++}$ | y* | y*$^{++}$ | # |
|---|---|---|---|---|---|---|---|---|---|---|
| 1 | 164.0706 | 82.5389 | | | Y | | | | | 11 |
| 2 | 372.1190 | 186.5631 | | | Y | 1377.6004 | 689.3039 | 1360.5739 | 680.7906 | 10 |
| 3 | 532.1497 | 266.5785 | | | C | 1169.5520 | 585.2797 | 1152.5255 | 576.7664 | 9 |
| 4 | 679.2181 | 340.1127 | | | F | 1009.5214 | 505.2643 | 992.4948 | 496.7511 | 8 |
| 5 | 807.2767 | 404.1420 | 790.2501 | 395.6287 | Q | 862.4530 | 431.7301 | 845.4264 | 423.2169 | 7 |
| 6 | 864.2981 | 432.6527 | 847.2716 | 424.1394 | G | 734.3944 | 367.7008 | 717.3679 | 359.1876 | 6 |
| 7 | 978.3410 | 489.6742 | 961.3145 | 481.1609 | N | 677.3729 | 339.1901 | 660.3464 | 330.6768 | 5 |
| 8 | 1106.3996 | 553.7034 | 1089.3731 | 545.1902 | Q | 563.3300 | 282.1686 | 546.3035 | 273.6554 | 4 |
| 9 | 1253.4680 | 627.2377 | 1236.4415 | 618.7244 | F | 435.2714 | 218.1394 | 418.2449 | 209.6261 | 3 |
| 10 | 1366.5521 | 683.7797 | 1349.5256 | 675.2664 | L | 288.2030 | 144.6051 | 271.1765 | 136.0919 | 2 |
| 11 | | | | | R | 175.1190 | 88.0631 | 158.0924 | 79.5498 | 1 |

Fig. 9

Sequences of heme binding regions of hemopexins

Using the rabbit hemopexin precursor sequence (UniProtKB #P20058),
the heme binding histidine residues are 238 and 291 (H)

```
SEQ ID NO 13 rabbit   LDVRDYFLSC  PGRGH---R-  SS-HRNSTQH  GHESTRCDPD
SEQ ID NO 14 human    RDVRDYFMPC  PGRGHGH-RN  GTGHGNSTHH  GPEYMRCSPH
SEQ ID NO 15 rat      LDARDYFISC  PGRGHGKLRN  GTAHGNSTHP  --MHSRCNAD
SEQ ID NO 16 pig      RDVRDYFMSC  PGRGHAH-RN  AT-HRGDD--  -----RCSPD
SEQ ID NO 17 mouse    LDARDYFVSC  PGRGHGRPRN  GTAHGNSTHP  --MHSRCSPD SEQ ID NO 13 rabbit   LVLSAMVSDN  HGATYVFSGS  HYWRLDTNRD  GWHSWPIAHQ
SEQ ID NO 14 human    LVLSALTSDN  HGATYAFSGT  HYWRLDTSRD  GWHSWPIAHQ
SEQ ID NO 15 rat      PGLSALLSDH  RGATYAFSGS  HYWRLDSSRD  GWHSWPIAHH
SEQ ID NO 16 pig      LVLTALLSDN  HGATYAFRGT  HYWRLDTSRD  GWHSWPIDHQ
SEQ ID NO 17 mouse    PGLTALLSDH  RGATYAFTGS  HYWRLDSSRD  GWHSWPIAHH
```

Fig. 10

Hemopexin sequence alignment for PDB 1QHU (SEQ ID NO 18) and rabbit hemopexin precursor sequence (SEQ ID NO 19) (UniProtKB accession # P20058)

Bold/Underlined = signal peptide
Gray highlight = missing from structure (Paoli ref)

```
                              1                                              24
1QHU    -25 ---------- ---------- ---------- ---------- ---------IE
P20058    1 MVKASGIPIA LGVWGLCWSL ATVNSVPITS AHGNVTEGES GTKEEADVIE

1QHU     26 QCSDGWSFDA TTLDDNGTML FFKDEFVWKS HRGIRELISE RWKNFIGPVD
P20058   51 QCSDGWSFDA TTLDDNGTML FFKDEFVWKS HRGIRELISE RWKNFIGPVD
                                            98         106
1QHU     76 AAFRHGHTSV YLIKGDKVWV YTS------- ---PKSLQDEFPG IPFPLDAAVE
P20058  101 AAFRHGHTSV YLIKGDKVWV YTSEKNEKVY PKSLQDEFPG IPFPLDAAVE

1QHU    126 CHRGECQDEG ILFFQGNRKW FWDLTTGTKK ERSWPAVGNC TSALRWLGRY
P20058  151 CHRGECQDEG ILFFQGNRKW FWDLTTGTKK ERSWPAVGNC TSALRWLGRY
                                                     215        222
1QHU    176 YCFQGNQFLR FNPVSGEVPP GYPLDVRDYF LSCPGRGHRS -------HGH
P20058  201 YCFQGNQFLR FNPVSGEVPP GYPLDVRDYF LSCPGRGHRS SHRNSTQHGH

1QHU    225 ESTRCDPDLV LSAMVSDNHG ATYVFSGSHY WRLDTNRDGW HSWPIAHQWP
P20058  251 ESTRCDPDLV LSAMVSDNHG ATYVFSGSHY WRLDTNRDGW HSWPIAHQWP

1QHU    275 QGPSTVDAAF SWEDKLYLIQ DTKVYVFLTK GGYTLVNGYP KRLEKELGSP
P20058  301 QGPSTVDAAF SWEDKLYLIQ DTKVYVFLTK GGYTLVNGYP KRLEKELGSP

1QHU    325 PVISLEAVDA AFVCPGSSRL HIMAGRRLWW LDLKSGAQAT WTELPWPHEK
P20058  351 PVISLEAVDA AFVCPGSSRL HIMAGRRLWW LDLKSGAQAT WTELPWPHEK

1QHU    375 VDGALCMEKP LGPNSCSTSG PNLYLIHGPN LYCYRHVDKL NAAKNLPQPQ
P20058  401 VDGALCMEKP LGPNSCSTSG PNLYLIHGPN LYCYRHVDKL NAAKNLPQPQ

1QHU    425 RVSRLLGCTH
P20058  451 RVSRLLGCTH
```

Fig. 11

Table 1

| HPX species | NCBI gi number | SEQ ID NO | Peptide sequence | $Y^n$ site | Charge (+) | Sequest XCorr | Mascot ions score |
|---|---|---|---|---|---|---|---|
| Homo sapiens | 1321561 | SEQ ID NO 1 | $^{198}YY^nCFQGNQFLR^{208}$ | 199 | 2 | 3.068 | 77.1 |
| Rabbit | 130500366 | SEQ ID NO 2 | $^{118}VWVY^nTSEK^{125}$ | 121 | 2 | 2.100 | 34.7 |
| Rabbit | 130500366 | SEQ ID NO 3 | $^{200}YY^nCFQGNQFLR^{210}$ | 201 | 2 | 4.576 | 67.5 |
| Rabbit | 130500366 | SEQ ID NO 5 | $^{228}DY^nFLSCPGR^{236}$ | 229 | 2 | 2.225 | 50.8 |
| Rabbit | 130500366 | SEQ ID NO 6 | $^{316}LY^nLIQDTK^{323}$ | 317 | 2 | 2.796 | 68.6 |
| Rabbit | 130500366 | SEQ ID NO 7 | $^{324}VY^nVFLIK^{330}$ | 325 | 2 | 2.601 | 52.5 |
| Rat | 123036 | SEQ ID NO 9 | $^{117}YY^nCFQGNK^{204}$ | 118 | 2 | 2.507 | 46.9 |

*Fig. 12*

*Table II*

| HPX species | NCBI gi number | SEQ ID NO | Peptide sequence | COM site | Charge (+) | Mascot ions score |
|---|---|---|---|---|---|---|
| Rabbit | 130500366 | SEQ ID NO 2 | $^{118}$VW*VYTSEK$^{125}$ | 119 | 2 | 39.3 |
| Rabbit | 130500366 | SEQ ID NO 3 | $^{200}$YY$^{188c}$CFQGNQFLR$^{210}$ | 201 | 2 | 51.1 |
| Rabbit | 130500366 | SEQ ID NO 4 | $^{211}$FNPVSGEVPPGY$^{c}$PLDVR$^{227}$ | 222 | 2 | 69.8 |
| Rabbit | 130500366 | SEQ ID NO 5 | $^{228}$DY$^{188c}$FLSCPGR$^{236}$ | 229 | 2 | 25.1 |
| Rabbit | 130500366 | SEQ ID NO 8 | $^{331}$GGYTLVNGY$^{c}$PK$^{341}$ | 339 | 2 | 47.6 |

Fig. 13

Table III

| HPX species | NCBI gi number | SEQ ID NO | Peptide sequence | COM site | Charge (+) | Mascot ions score |
|---|---|---|---|---|---|---|
| Rabbit | 130500366 | SEQ ID NO 4 | $^{211}$FNPVSGEVPPGY$^{\text{di-C}}$PLDVR$^{227}$ | 222 | 2 | 63.3 |
| Rabbit | 130500366 | SEQ ID NO 4 | $^{211}$FNPVSGEVPPGY$^{\text{tri-Bu}}$PLDVR$^{227}$ | 222 | 2 | 39.3 |
| Rabbit | 130500366 | SEQ ID NO 5 | $^{228}$DY$^{\text{C}}$FLSCPGR$^{236}$ | 229 | 2 | 30.6 |
| Rabbit | 130500366 | SEQ ID NO 5 | $^{228}$DY$^{\text{di-C}}$FLSCPGR$^{236}$ | 229 | 2 | 31.8 |

Fig. 14

Table IV

| Amino acid | Covalent oxidative modifications | | | | |
|---|---|---|---|---|---|
| Y121 | nitration | | | | |
| Y201 | nitration | tBu | | | |
| Y222 | nitration | mono-Cl | | [di-Cl] | [tBu] |
| Y229 | nitration | tBu | [mono-Cl] | [di-Cl] | |
| Y317 | nitration | | | | |
| Y325 | nitration | | | | |
| Y339 | | mono-Cl | | | |
| W119 | | oxidation | | | |

ASSAY FOR NITRATED AND TOTAL HEMOPEXIN IN FLUID SAMPLES

CROSS-REFERENCE TO RELATED APPLICATIONS

This application claims the benefit of U.S. Provisional Patent Application Ser. No. 62/088,920 filed Dec. 8, 2014, which is incorporated by reference herein.

GOVERNMENT LICENSE RIGHTS

This invention was made with government support under grant number NIH R21 DK064363 (A.S.) awarded by the National Institute of Health. This invention was also made with governmental support under a Faculty Research Grant (A.S.) and Research Incentive Funds (A.S.) from the University of Missouri, Kansas City, Mo. The governments have certain rights in the invention. Applicant hereby requests all available rights to the invention that are not reserved for the governmental entities.

BACKGROUND OF THE INVENTION

Heme is a chemically reactive biological form of iron that may be toxic and pathogenic in certain clinical conditions, such as acute and chronic hemolysis, stroke, cerebral hemorrhage, sickle cell disease (SCD), shock and sepsis. Heme is also released by mechanical lysis of red blood cells during prolonged extracorporeal circulation for cardiac surgery or when heart valves malfunction. Hemopexin (HPX) is a heme binding protein that protects cells against these toxic effects of heme. The name hemopexin means heme fixer or grabber and when this protein binds heme in a 1:1 stoichiometric complex, we term it heme-HPX. Thus, as used herein, the terms HPX and apo-HPX refer to the protein, hemopexin, itself (not "pexin"). This nomenclature differs from that used for hemoglobin, which refers to heme bound to the protein, globin. Significantly, HPX can be inactivated, or lose its heme-binding ability, after exposure to conditions that generate reactive nitrogen species (RNS), which nitrate certain amino acids residues, e.g. tyrosine. Nitration of HPX reduces the levels of active HPX in the blood plasma and other biological fluids (e.g. cerebrospinal fluid, CSF) and allows heme toxicity to develop. Evidence supports that chemically-modified hemopexin, which has the heme coordinating histidines inactivated, remains in the circulation, and presumably also in other biological fluids like CSF, and is not rapidly cleared.

Many proteins are inactivated by oxidative modification(s), and we considered that the heme binding by hemopexin might become impaired in inflammation when reactive oxygen species (ROS) including hypochlorous acid (HOCl) are present. The potential for damage to hemopexin was revealed by our recent in vitro studies showing that the heme-hemopexin complex was highly resistant to oxidative damage from peroxides and HOCl compared with the apoprotein but high amounts of ROS in vitro were required. We investigated whether there is damage to HPX from RNS because in inflammatory conditions both ROS and RNS are present. For example, activated neutrophils produce their defensive "respiratory burst" of reactive oxygen intermediates; and endothelial cells, macrophages and astrocytes produce nitric oxide (NO.) after immunological or inflammatory stimuli. We have discovered that human (*Homo sapiens*), rabbit (*Oryctolagus cuniculus*), and rat (*Rattus norvegicus*) HPX isolated from plasma using standard techniques contain low levels of endogenous nitrated tyrosines. Using liquid chromatography-tandem mass spectrometry (LC-MS/MS), we identified a predominant nitrated tyrosine that resides in the peptide YY"CFQGNQFLR (SEQ ID NO 1), and which is conserved in human, rabbit and rat HPX. Immuno-blotting and selective reaction monitoring were used to quantitate the extent of nitration of HPX after myeloperoxidase/glucose oxidase (MPO/GO) treatment an in vitro system that mimics oxidative stress with RNS. Significantly, heme binding by HPX is increasingly impaired as tyrosine nitration proceeds and two of the three nitrated tyrosines identified by our analysis reside in the heme binding site and interact directly with the heme. Importantly, nitration is an event requiring a specific environment around the tyrosine residue and lack of steric hindrance since this amino acid is often embedded within the hydrophobic core of the protein and protected from nitration. Thus, nitration of tyrosine residues is selective and such specificity strongly supports the concept that these amino acids are a preferential target for biological events in vivo.

Oxidative stress is linked to the development of neurodegeneration in the brain and inflammation is considered to contribute to the early stages of Alzheimer's disease (AD) to which HPX has been linked. Furthermore, brain iron increases in AD and in HPX-knockout mice as they age. We have previously shown that three models of ROS, namely $H_2O_2$, tert-butyl hydroperoxide and hypochlorous acid can impair heme binding by HPX, although high molar ratios of ROS:HPX are needed, generally supra-physiological. Here, we identify covalent oxidative modifications (COMs) of apo-HPX after exposure to these ROS. The term COM is used rather than post-translational modifications because COMs affect the mature, secreted HPX rather than the post-translational modifications that occur during the synthesis and secretion of HPX. Several tyrosine residues that reside in the heme binding site were targeted for modification by more than one oxidant and, thus, constitute susceptible targets for damage in vivo. In contrast, the heme-HPX complex is fairly resistant to damage by ROS, as previously shown and is shown here to be relatively resistant to nitration by MPO/GO. Even when heme-HPX is exposed to $H_2O_2$ or tert-butyl hydroperoxide, it still delivers heme for heme oxygenase-1 induction that is cytoprotective. Inactivation of apo-HPX in plasma or other biological fluids by oxidative modification likely occurs close to activated endothelial and immune system cells, which are the sites of production of RNS and ROS.

It has been shown that HPX loses this protective biological function when exposed to nitrating species in systems that mimic the oxidative environment of inflammation expected in sickle cell disease, shock and sepsis or in the brain after damage. Accordingly, HPX can be used as a biomarker for conditions of oxidative stress in which nitration of protein molecules has been detected including neurodegeneration (i.e., mild cognitive impairment (MCI) and Alzheimer's disease (AD)); in systemic inflammatory responses (i.e., acute lung injury, SCD, sepsis, shock and multiple organ failure syndrome); and is also of importance for neonates and children with hemolytic conditions and sepsis who are more at risk than adults due to their low basal levels of HPX. Further, two independent studies have shown that low levels of HPX in humans correlate with high risk of dying from sepsis.

It has been demonstrated that heme toxicity due to HPX depletion in mouse models of SCD and sepsis can be rescued by HPX supplementation. Thus, treatment with HPX infusions can aid in recovery and improve clinical outcomes in clinical SCD crisis and sepsis among other conditions. Nitration of HPX, which inactivates HPX's heme-binding ability, likely precedes its depletion because photo-inactivated HPX with altered heme coordinating histidine residues remains in the circulation. Low levels of HPX in humans when diagnosed with sepsis correlates with a high risk of dying and HPX supplementation in a mouse model of sepsis decreases the death rate from 80 to 20%. Plasma protein therapy is established for human serum albumin as a plasma expander to stabilize blood pressure in shock or sepsis and for immunoglobulins in certain immuno-deficiency states. HPX replenishment therapy is under consideration for commercial development. Current techniques measure solely total levels of HPX, which can underestimate the amount of active HPX. Therefore, there is a need for a sensitive and accurate assay for detecting the levels of nitrated HPX in samples of body fluid such as serum, plasma, cerebral spinal fluid and lung aspirate. Such information together with total HPX levels will allow a better understanding of the patients' risk of developing HPX deficiency and aid in diagnosis as well as in the timing of replenishment infusions.

SUMMARY OF THE INVENTION

There is a need for an accurate, yet simple and inexpensive, test or assay to detect levels of nitrated HPX in fluid samples collected from subjects since this represents inactivated HPX that cannot bind heme. The present invention provides a nitrated HPX biomarker and an enzyme-linked immunosorbant assay (ELISA) for detecting increased levels of nitrated HPX in at-risk patients before a HPX deficiency state develops. The ELISA of the present invention is a two-site sandwich technique that both detects and measures both nitrated and non-nitrated (i.e., native or unmodified) HPX in biological fluids such as serum, plasma, cerebral spinal fluid and lung aspirate. Furthermore, it is anticipated that in the foreseeable near future additional and alternative methodologies will be available to develop this assay concept as a diagnostic as described in sections [0040]-[0045].

The ELISA of the present invention is a relatively cheap, simple and straightforward assay that can monitor HPX as a biomarker for several disease states including shock, SCD, sepsis and hemolytic states (e.g. hemolysis, after and during prolonged extracorporeal circulation of blood for surgery or hemorrhagic Ebola). Early diagnosis of these diseases would enable therapeutics (e.g. HPX infusions) to be administered to treat a variety of diseases and iatrogenic conditions.

Although septic shock is different from hemorrhagic shock, it is likely that HPX deficiency states occur in hemorrhagic shock that can develop after Ebola, Dengue and Marburg viral infection. The kidney is the organ the helps to retain heme and its iron and especially needs protection. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2A illustrates the structure of the heme-hemopexin complex. When human hemopexin is threaded on the rabbit hemopexin crystal structure (generated in PyMOL from PDB file 1QHU), the nitrated tyrosine $Y''_{199}$ in the human sequence (labeled and shown as black ring structures) is equivalent to $Y''_{201}$ in rabbit. Nitration of this tyrosine after incubation of hemopexin with MPO/GO is conserved in human, rabbit, and rat protein. Also shown are the heme-iron coordinating histidine residues; the receptor binding site (loop of Jen 14 epitope) and the linker peptide (dashed black line). The linker is modeled on the amino acid backbone because there was insufficient electron density in the crystal structure. FIG. 2B is a close-up view of the amino acid resides in the heme binding site of the heme-hemopexin complex; in particular, the two tyrosine residues that are endogenously nitrated (Tyr 201 and Tyr 222), which interact directly with the propionate group on the D-ring of the heme and contribute with other aromatic resides to the hydrophobic environment around the heme. Tyr 201 and Tyr 222 help surround the propionate together with Arg 199 and Arg 210 from the N-domain and three histidine residues from the C-domain (not shown). FIG. 2C illustrates the endogenously nitrated tyrosine residues in rabbit hemopexin identified by LC-MS/MS and summarized in Table I (below).

FIGS. 3A through 3E illustrate that in vitro nitration of human HPX targets tyrosines and preferentially $Y_{199}$. FIGS. 3A.1 and 3B.1 are Western immuno-blots showing the rate of appearance of nitrotyrosine (Y") in human hemopexin after incubation with MPO/GO detected by immuno-blotting with an anti-3'Y" antibody as described in the methods section, wherein the membrane was stripped and reprobed with polyclonal goat anti-human hemopexin. FIGS. 3A.2 and 3B.2 are graphs illustrating the time course of MPO/GO treatment corresponding to the Western immune-blots of FIGS. 3A.1 and 3B.1. FIG. 3C compares four chromatographic spectra showing the chromatographic peaks from selected reaction monitoring (SRM) analysis for human hemopexin after 120 min incubation with MPO/GO are shown for the: (i) base peak, (ii.) nitrated peptide, YY"CFQGNQFLR (SEQ ID NO 1), unmodified peptide, (iii.) YYCFQGNQFLR (SEQ ID NO 1), and internal reference peptide, (iv.) NFPSPVDAAFR (SEQ ID NO 10) for normalizing. The peaks were quantified by integration using the native reference peptide method. The two minor peaks in the un-modified peptide mass chromatogram that appear to the right of the major peak (spectrum ii) are unrelated ions with the same m/z, coincidentally. These did not interfere with, and were not included in the peak area integration for quantitative analysis. FIG. 3D is a graph illustrating the time course of nitration using SRM data that were quantitated using chromatographic peak areas of the modified peptide at each time point were corrected by the reference peptide. The average peak ratio (nitrated/internal reference) of three separate gel excisions and analysis per time point is shown +/−S.D. FIG. 3E is a graph illustrating the standardization of the synthetic peptides using the 2,4,6-trinitrobenzenesulfonic acid method of peptide concentration determination. Standard curves were calibrated using chromatographic peak areas for peptides at each concentration point. Experimental chromatographic peak area ratios were obtained by dividing the reference peptide peak area by either the YY"CFQGNQFLR (SEQ ID NO 1) or the YYCFQGNQGLR (SEQ ID NO 1) peptide and then plotted versus the known mole ratio of the peptides. Mole fractions were found by dividing the concentration of the NFPSPVDAAFR (SEQ ID NO 10) peptide by concentrations of either the YY"CFQGNQFLR (SEQ ID NO 1) or YYCFQGNQGLR (SEQ ID NO 1) peptides ranging from 10-90 µM. The standard curves produced the following equations: y=1368x−29.98 (YY"CFQGNQFLR) and y=1298x−109.8 (YYCFQGNQGLR, generated by 6 linear regression software sold under the trade name GraphPad Prism by GraphPad Software, Inc. La Jolla, Calif. USA). The mole ratio for nitration increased with time of incubation with the MPO/GO nitrating system.

FIGS. 4A and 4B shows three graphs that illustrate that human apo-HPX is more susceptible to nitration than the heme-HPX complex and tyrosine nitration inhibits heme binding by HPX. FIG. 4A is a graph showing test results when human apo-hemopexin (triangles) and heme-hemopexin (squares) were treated with myeloperoxidase/glucose oxidase-mediated nitration as for FIGS. 3A.1 and 3B.1 followed by immuno-blotting and the signal intensity of nitrated protein relative to total protein, was quantitated using UN-SCAN-IT gel and normalized to the time zero samples. Higher nitration of apo-hemopexin is apparent within 10-15 minutes incubation at 37° C. After 2 hours, apo-hemopexin was nitrated ~2.6-fold more than heme-hemopexin. To more readily distinguish this difference, the concentrations of MPO/GO nitrating reagents, relative to protein, were decreased by 75%. FIG. 4B is a graph showing test results when the reaction mixtures were prepared as described in FIG. 2A to produce nitrated (plus glucose) and control (minus glucose) apo-hemopexin. Excess glucose was removed from aliquots as described in the methods section. After concentration, heme binding on each of the aliquots of hemopexin (diluted to 7 µM in PBS) was carried out by addition of 0.9 molar equivalents of heme. The amount of heme bound to nitrated hemopexin (open squares) was determined (after 20 min on ice) from the absorbance in the Soret region (406 nm) using our standard procedures (39) and compared with control hemopexin (open triangles) treated in parallel. Over about 90 min, nitration of hemopexin progressively impaired heme binding.

FIG. 5A illustrates amino acid residues that were solely endogenously nitrated ($Y_{317}$ and $Y_{325}$) shown in black, those that were modified by ROS ($Y_{222}$ and $Y_{339}$) are shown in light grey and those modified by both nitration and ROS ($Y_{201}$ and $Y_{229}$) are shown in medium grey. Notably, tyrosines 201, 222, and 229 all reside in the heme binding site consistent with the impaired heme binding and are clearly vulnerable to oxidative modification unless protected by heme binding. Also identified were tryptophan 119 and tyrosine 121 in the N-domain; and tyrosines 317, 325 and 339 in the C-domains (see Tables II and III). The peptides in which the three modified tyrosines in the N- and C-domains reside are contiguous; however, they are in different blades of the two homologous β-propellor domains. The relative conformation of the two domains in the open apo-protein structure is unknown as is the site of attachment of the N-linked carbohydrate chains. The modified residues are no longer solvent accessible when heme is bound to hemopexin i.e. in the heme-hemopexin complex although the receptor binding site appears exposed as expected. FIG. 5B When the N- (wheat) and C- (blue/grey) homologous β-propellor domains of hemopexin are superimposed (N- to C-orientation), the three oxidatively modified tyrosine residues in the heme binding site reside on blade 4 (BL4) whereas the three on the C-domain reside on blade 6 (BL6). The blades are numbered sequentially from the N- to C-terminus of hemopexin with blades 1-4 on the N-domain and blades 5-8 on the C-domain.

FIG. 8 is a table of Mascot search results for nitration of human hemopexin in vivo. The following are the results of a recent Mascot search of the same data file (05Dec1316.raw) and scan (2173), which identified the same peptide YY"CFQGNQFLR (SEQ ID NO 1). The monoisotopic mass of the neutral peptide is 1539.6565 Da.

FIG. 11 shows Table I which provides test results for identification using LC-MS/MS of peptides with nitrated tyrosine residues in hemopexin isolates from human, rabbit and rat plasma. Quantifiable nitration in hemopexin was detected on a few conserved tyrosines as described in the Methods section. The predominant nitrotyrosine (Y") identified was a conserved tyrosine in the tryptic peptide YY"CFQGNQFLR (SEQ ID NO 1) from human ($Y_{199}$), rabbit ($Y_{201}$), and YY"CFQGNK (SEQ ID NO 9) from rat ($Y_{118}$) hemopexin. Also shown are four additional nitrated tyrosines identified in rabbit hemopexin. These data were obtained from two human plasma samples, three separate pooled rabbit sera samples and one pooled rat serum. One human hemopexin isolate lacked detectable nitration.

FIG. 12 shows Table II which provides the data for the identification of chlorinated and butylated tyrosines and an oxidized tryptophan in peptides of ROS-treated rabbit hemopexin using LC-MS/MS. These modified amino acids in five peptides were unambiguously detected and identified using MASCOT. HPX:ROS ratios were 1:10 HOCl (VW$^{ox}$VYTSEK (SEQ ID NO 2), FNPVSGEVPPGY$^{Cl}$-

Figure 1:
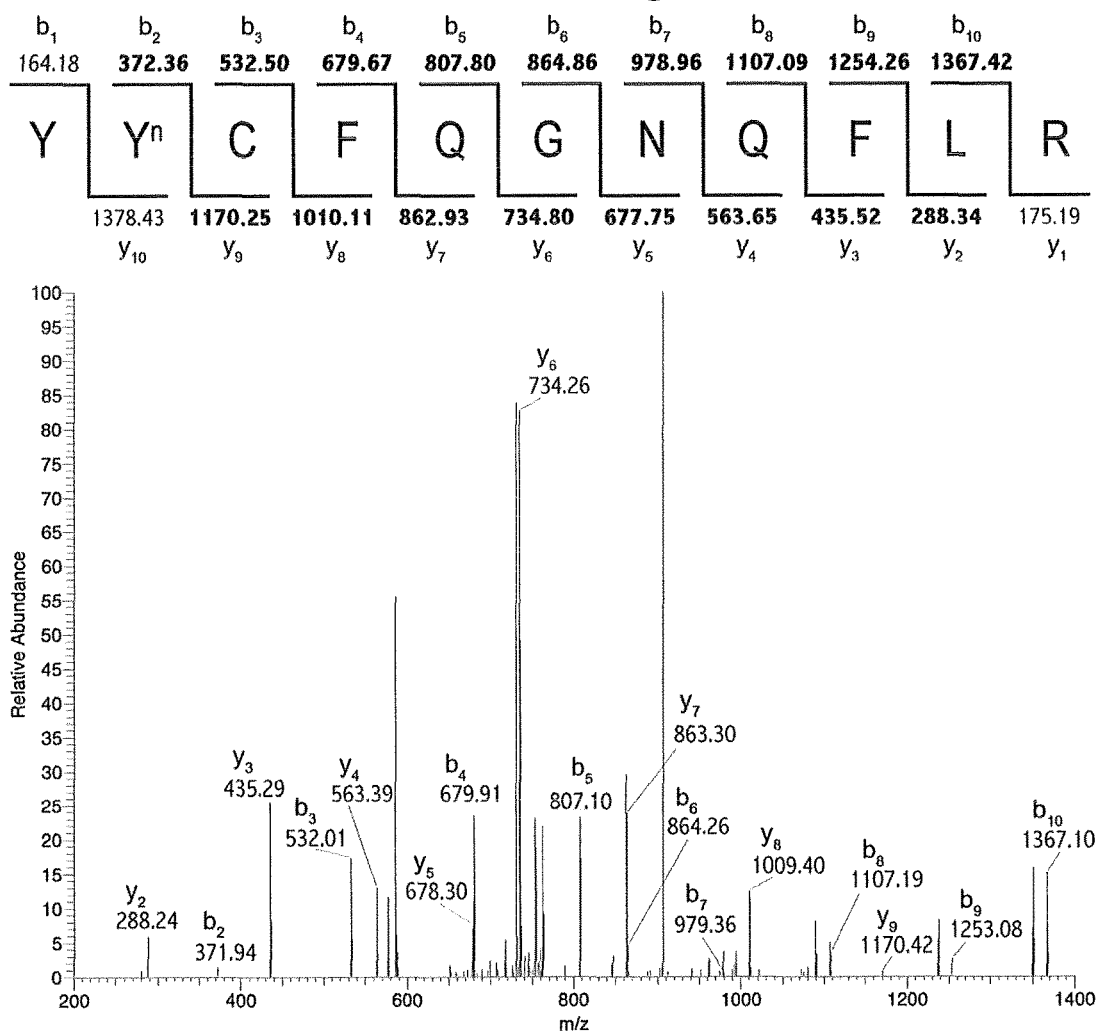
FIG. 1 is a spectrograph illustrating that nitration of human hemopexin occurs in vivo at $Y_{199}$ wherein tyrosine nitration was detected by LC-MS/MS analysis of hemopexin isolated from human plasma, and a tandem mass spectrometry data analysis program for protein identification known by the trade name SEQUEST (The Scripps Research Institute, La Jolla, Calif., USA) was used to identify $Y''_{199}$ on the tryptic peptide YY"CFQGNQFLR (SEQ ID NO 1) (see Table I below for XCorr value). Matched b and y ions are shown in bold in the ions diagram (above) and are indicated next to corresponding peaks in the MS/MS spectrum (below). Similar high quality spectra were obtained from rabbit hemopexin (FIG. 6) and rat hemopexin (FIG. 7).

PLDVR (SEQ ID NO 4), GGYTLVNGY$^{Cl}$PK (SEQ ID NO 8)); 1:2.5 tBuOOH (YY$^{tBu}$CFQGNQFLR (SEQ ID NO 3)); and 1:1 tBuOOH (DY$^{tBu}$FLSCPGR (SEQ ID NO 5)). Superscripts indicate residues modified by oxidation (ox), t-butylation (tBu), or mono-chlorination (Cl).

FIG. 13 shows Table III which provides data with regard to peptides with additional oxidative-modifications of tyrosine residues identified by LC-MS/MS after incubation of rabbit hemopexin with tBuOOH and HOCl. These modified peptides were unambiguously identified by MASCOT with the tyrosine modifications shown, based on mass difference, but the particular amino acid was not validated. HPX:ROS ratios were 1:10 HOCl (FNPVSGEVPPGY$^{di-Cl}$PLDVR (SEQ ID NO 4), DY$^{Cl}$FLSCPGR (SEQ ID NO 5), DY$^{di-Cl}$FLSCPGR (SEQ ID NO 5)), and 1:1, 1:2.5, and 1:10 tBuOOH (FNPVSGEVPPGY$^{tBu}$PLDVR (SEQ ID NO 4)). Mascot scores for FNPVSGEVPPGY$^{tBu}$PLDVR (SEQ ID NO 4) from 1:1 and 1:2.5 tBuOOH searches were 39.2 and 32.8, respectively. Superscripts indicate residues modified by t-butylation (tBu), mono- (Cl) or di-chlorination (di-Cl).

FIG. 14 shows Table IV which provides a summary of data illustrating the covalent oxidative modifications of amino acids of rabbit hemopexin, in particular that the endogenous nitration of $Y_{201}$ (rabbit) is conserved on $Y_{199}$ (human) and $Y_{118}$ (rat). Significantly, in the 3D-crystal structure of hemopexin, $Y_{201}$ and $Y_{222}$ interact with the propionate oxygen of heme ring D, and $Y_{229}$ also resides near the bound heme and see FIG. 2B. There were several additional nitration sites, $Y_{121}$, $Y_{317}$ and $Y_{325}$. The amino acids and their modifications that were not unambiguously identified by MASCOT, summarized in Table III, are shown in square brackets.

FIG. 9 is an alignment of the amino acid sequences of heme binding regions of hemopexin from rabbit, human, rat, pig and mouse, illustrating the amino acid conservation between species.

FIG. 10 is a hemopexin amino acid sequence alignment for PDB 1QHU and rabbit hemopexin precursor sequences (UniProtKB accession # P20058).

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Definitions

The term "human hemopexin" or "human HPX" as used herein is a broad term, and is to be given its ordinary and customary meaning to a person of ordinary skill in the art (and it is not to be limited to a special or customized meaning), and refers without limitation to a polypeptide with the amino acid sequence of GenBank Accession No. AAA58678 (*Homo sapiens*) or NP.sub.-000604 (*Homo sapiens*). Hemopexin is a glycoprotein comprised of a polypeptide chain with several carbohydrate chains covalently attached. "Native hemopexin" or "native HPX" refers to an un-modified hemopexin full length polypeptide that has not been modified by nitration of at least one amino acid.

"Nitrated hemopexin" or "nitrated HPX" refers to a hemopexin full length polypeptide that has at least one nitrated amino acid; and a nitrated HPX peptide refers to proteolytic fragments of nitrated HPX that have at least one nitrated amino acid. For example, the nitrated hemopexin is modified by nitration on at least one tyrosine residue, such as tyrosine 199 (i.e., $Y''_{199}$), tyrosine 201 (i.e., $Y''_{201}$), tyrosine 222 (i.e., $Y''_{222}$) and tyrosine 229 (i.e., $Y''_{229}$), depending upon the species of animal, such as is described below in greater detail. These nitrated tyrosine residues are generally located in the heme binding center of the hemopexin molecule. Using methods known in the art, an antibody can be raised or otherwise created, wherein the antibody detects one of native hemopexin plus nitrated hemopexin, native hemopexin but not nitrated hemopexin, and nitrated hemopexin; or in certain assays the antibody detects native hemopexin and one or more other antibodies nitrated peptides of hemopexin.

The term "subject" as used herein is a broad term, and is to be given its ordinary and customary meaning to a person of ordinary skill in the art (and it is not to be limited to a special or customized meaning), and refers without limitation to a vertebrate, such as a mammal, e.g., a human. Mammals include, but are not limited to, farm animals (such as cows), sport animals, pets (such as cats, dogs, and horses), mice, rats, mini-pigs and primates. Desirably, the subject is a human such as an adult human, a newborn or a premature infant, or children 1-10 years.

The term "fluid sample" as used herein is a broad term, and is to be given its ordinary and customary meaning to a person of ordinary skill in the art (and it is not to be limited to a special or customized meaning), and refers without limitation to liquids originating from inside the bodies of living people. They include fluids that are excreted or secreted from the body as well as body water that normally is not. Exemplary fluids include blood, saliva, urine, CSF, body tissue and tissue fluids (bronchial lavage).

Throughout this specification and claims, the word "comprise," or variations such as "comprises" or "comprising," will be understood to imply the inclusion of a stated integer or group of integers but not the exclusion of any other integer or group of integers.

Nitrated Hemopexin and Total Hemopexin Assay

The present invention is based on the inventors' discovery that endogenous levels of tyrosine nitration predominantly on tyrosine 199 of human HPX in the peptide YYCFQGNQFLR (SEQ ID NO 1), all of which are conserved in rabbit and rat hemopexin. Significantly, heme binding by HPX became increasingly impaired as tyrosine nitration proceeds and several nitrated tyrosines, including tyrosine 199, reside in the heme binding site and interact directly with the heme. These additional tyrosines identified in rabbit hemopexin are tyrosine 222, 229 and, others in the C-terminus tyrosines 317 and 325; all are conserved in human hemopexin and thus are additional potential targets. The present invention is directed to an ELISA that detects nitrated HPX in fluid samples from subjects at risk of heme toxicity in sepsis, SCD, shock and hemorrhagic diseases.

HPX is a glycoprotein that binds heme very tightly (Kd less than picomolar) and administration of purified HPX or recombinant HPX reduces mortality in mouse model of sepsis and clinical sepsis as well as alleviating the potentially lethal vaso-occlusion and lung pathology in mouse models of SCD. The physiological function of HPX requires its intact molecular structure, although the deglycosylated protein still binds heme. The carbohydrate chains, together with at least one receptor binding site, likely play a role in receptor recognition before uptake of heme-HPX complexes by endocytosis. Heme binding to HPX causes a large change in conformation that generates receptor recognition sites needed to remove heme-HPX from biological fluids.

We have found that nitration of key tyrosine residues in a hierarchy of sites located in only a few regions of the protein impairs heme binding. An assay that determines only the levels of HPX may over-estimate the heme-binding activity of the protein and, thus, may underestimate the protective biological activity of HPX in a test sample of biological fluids from patients.

Human Hemopexin Biomarker

Native HPX from biological fluids may not allow access of the anti-Y‴ antibody or the smaller anti-Y‴ Fab fragment although some molecules of antigen can denature when attached to a solid support as during an ELISA reaction. Evidence supports that the two beta-propellor domains of HPX are expected to be stable. However, it is also possible that some immunizing preparations or clinical samples may contain some denatured molecules of HPX and additionally or alternatively oxidized forms. An alternative approach is to carry out a protease digestion of HPX and nitrated (MPO/GO-treated) HPX to generate un-nitrated and nitrated HPX peptide fragments; we will then generate peptide and Y‴-peptide-specific monoclonal antibodies raised against these peptides using standard techniques and use these antibodies to detect HPX fragments in protease-treated patient samples.

The ELISA assay of the present invention, for detecting and measuring nitrated and total HPX uses the two-site "sandwich" technique, which is well known in the art. Microplates having wells are coated with anti-HPX antibodies and an anti-nitrated tyrosine specific antibody conjugated with horseradish peroxidase, or anti-Y‴-HRP, are provided. Assay standards, controls and patient samples, such as serum, EDTA-plasma or CSF, are added directly into the wells of a microplate. A quantity of the anti-Y‴-HRP is immediately added to each well, to form the sandwich. The two-site sandwich is then detected with substrate solution and timed reaction as is known in the art. A set of standards is also provided, and includes a series of HPX samples treated with MPO/GO for different periods of time in vitro to generate increasing amounts of nitration, wherein the extent of nitration on these HPX standards is established by Mass Spectroscopy, such as is known in the art. In parallel with testing the samples with the anti-Y‴-HRP, total HPX detected and quantitated by testing the samples using an HRP-linked antibody to normal HPX (i.e., not nitrated). Antibodies for use in the assay of the present invention can be raised using methods known in the art. Suitable antibodies include an antibody that recognizes both native and nitrated hemopexin, an antibody that recognizes only native hemopexin and an antibody that recognizes only nitrated hemopexin or nitrated hemopexin peptides. For example, a first antibody that detects the amino acid sequence YY‴CFQGNQFLR (SEQ ID NO 1) from nitrated human hemopexin can be created. In another example, a second antibody that detects the amino acid sequence YYCFQGNQFLR (SEQ ID NO 1) from non-nitrated human hemopexin can be created.

The data generated by the ELISA of the present invention provides total HPX levels and nitrated HPX levels in the patient sample. These data indicate the presence or absence of a deficiency state (i.e. low levels of total HPX), and an indication of the heme binding activity of the HPX, wherein increased levels of nitrated HPX are indicative of reduced heme binding.

Given the finite possibility that the nitrated tyrosines of HPX are located in one or more non-contiguous epitopes, it is foreseen that alternative approaches include methods that use denatured HPX such as western immune-blots, LC-MS/MS immunoassays and multi-plexing immunoassays for detecting, measuring and comparing nitrated and native hemopexin in a biological fluid sample of a subject. For example, a method of detecting and measuring nitrated hemopexin and native hemopexin in a sample of a subject includes performing an assay on the sample and controls to detect native hemopexin and nitrated hemopexin so as to obtain test results, wherein the assay is one of a western immune-blot, an LC-MS/MS immune assay and a multi-plexing immunoassay, and wherein the assay uses antibodies to each of native hemopexin and nitrated hemopexin; comparing the test results of the sample and controls; and determining if an amount of nitrated hemopexin in the sample is elevated relative to an amount of the total hemopexin (i.e., the amount of nitrated hemopexin plus the amount of native hemopexin) in the sample. For example, in some assays the antibodies are denatured so as to detect such non-contiguous epitopes.

In another ELISA of the present invention, a sufficient number of murine IgG coated microwell strips or wells are placed in a holder to run human HPX standards (i.e., nitrated and un-nitrated), controls such as buffer without added sample, and unknown samples are tested in duplicate. The standards, controls and patient samples are added into the designated microwells. Next, a quantity of a suitably diluted "tracer" antibody (e.g. anti Y‴-HRP at 1:20-1:500) to each well. The plate is sealed and incubated at room temperature, orbital shaking 170 rpm, for a period of 2 hours. At the end of the incubation, the content of each well is aspirated. The wells are then washed 5 times with a working wash solution, followed completely aspirating the content. Alternatively, an automated microplate washer can be used.

A quantity of ELISA HRP Substrate is added into each of the wells. The plate is then sealed and then covered with aluminum foil to avoid exposure to light, and then incubated at room temperature for 20 minutes. The aluminum foil and plate sealer are removed and a quantity of ELISA Stop Solution is added into each of the wells with gentle mixing.

A microplate reader or a fluorescence reader and fluorescent labeled antibody probes sold under the trade name Alexa-Fluor (Thermo Fisher Scientific, Rockford, Ill., USA) (at wavelength for the Fluor label) is used to read the absorbance at 450/650 nm within 10 minutes in a microplate.

It is foreseen that other ELISA-style assay methods may be used with the present invention. Immunodiagnostics is being accelerated using microarray ELISA-style assays with protein array (Chip) technology. Capture arrays carry affinity reagents that are primarily antibodies to detect and quantitate analytes in plasma/serum and other biological fluids. For diagnostics, the capture arrays allow multiple immunoassays to be carried out in parallel protein expression profiling (i.e. quantitate and compare the levels of hemopexin and nitrated HPX and HPX fragments/peptides in health and disease.)

The performance of ELISAs to detect protein biomarkers in biological samples can often be improved by using MULTI-ARRAY technology—a multiplexed immunoassay platform with very sensitive electrochemical luminescence (ECL) detection—sold under the trade name Meso Scale Discovery (MSD, Meso Scale Discovery, Rockville, Md., USA). MSDs multi-array technology had already been adopted by major pharmaceutical companies. The advantages of this platform include high reproducibility between different laboratories, high reliability, low matrix effects and sensitive, accurate, absolute quantitations often with minimal dilution of samples. Thus, these platforms allow the measurement of native levels of biomarkers in normal and diseased samples without multiple dilutions because the low detection limits of ECL provide up to five logs of linear dynamic range.

The measurement of multiple analytes from a single sample, which is known as multiplexing, thus includes the potential to expand the detection of total and nitrated hemopexin in a panel of biomarkers including cytokines, haptoglobin and microRNA. Such panels are foreseen to be needed to determine when haptoglobin or hemopexin infusions should be given in when hemopexin deficiency states develop complex conditions including sickle cell disease, hemorrhagic fevers, shock and sepsis. Hemopexin deficiency may also occur after multiple blood transfusions following trauma, accidents, extracorporeal surgery during cardiac surgery and also during chemotherapy. Signals from total HPX and nitrated HPX can readily be normalized to a particular protein, or cytokine, or metabolite, or microRNA.

At the cutting edge of new laboratory practice is the application of direct proteomics/MS approaches for biomarker diagnosis using MS analysis driven in quantitative MRM mode. This avoids the need for specific antibodies. A multiplexed analysis, which can analyze up to 100 proteins simultaneously, is carried out. MS is ideal technique to reliably detect and quantitate disease-related changes in targeted proteins. Drastic improvements are being made in the rate at which sample peptides are prepared and separated by liquid chromatography before MS analysis. Quantification is achieved by multiple reaction monitoring (MRM) MS assays. These experiments use the ESI of the peptides followed by two stages of mass selection, the first one selecting the mass of the intact peptide (parent ion) and the second one a specific fragment of the parent (MRM transitions). MRM assays coupled with isotope dilution MS have proved their utility for quantitative analysis of biomarkers.

In addition, the stable isotope standards and capture by anti-peptide antibodies (SISCAPA) approach exploits the use of immobilized anti-peptide antibodies to isolate specific peptides together with stable isotopically labeled versions of the same peptides prior to MRM analysis.

Additional and alternative technical ways forward are available to further develop the basis of the invention as a diagnostic. For example, as described in the introduction, at the cutting edge of new laboratory practice is the application of direct proteomics/MS approaches for biomarker diagnosis. MS is ideal technique to reliably detect and quantitate disease-related changes in targeted proteins and antibodies are not needed. HPX can be enriched in plasma samples and in other body fluids (since HPX has been detected in essentially all of them but sometimes at relatively low concentrations compared with plasma) using digital microfluidics coupled with MS. Ideally for a bedside diagnostic, the time from patient sampling to the analysis results should be only a few hours. Given the current interest in these automated and multiplexed array techniques, the speed of many of the steps of the analysis is expected to be significantly improved in the near future.

The following examples are meant to illustrate the invention and should not be construed as limiting.

EXAMPLES

Experimental Procedures

Materials

Sodium nitrite, sodium phosphate monobasic/dibasic, sodium chloride and glucose were obtained from Thermo Scientific (Rockford, Ill., USA); glucose oxidase, diethylene triamine pentaacetic acid (DTPA) and wheat germ lectin agarose from Sigma (St. Louis, Mo., USA); and myeloperoxidase from EMD Millipore Chemicals (Billerica, Mass., USA). Heme and mesoheme (iron mesoporphyrin chloride IX) were obtained from Frontier Scientific (Logan, Utah, USA).

Hemopexin Isolates

Native, glycosylated, human, rat and rabbit hemopexin were isolated and purified from plasma using our published procedures and plasma sources (8). After several differential precipitation steps, rabbit hemopexin was obtained by ion exchange chromatography (9) and human and rat hemopexin by affinity chromatography on wheat germ lectin resin by elution with N-acetyl d-glucosamine (10). Additional purification chromatography steps are now routinely carried out on an ÄKTA protein purification system (GE Life Sciences) using ion-exchange (mono Q and mono S resins) and size exclusion with Superdex. The purity of hemopexin (>99%) was assessed by SDS-PAGE and a Coomassie gel stain sold under the trade name Coomassie Gelcode Blue (Thermo Fisher Scientific, Rockford, Ill., USA). Stoichiometric 1:1 heme-hemopexin complexes (>90-95% saturated) were prepared and characterized as published (8) using heme/DMSO and keeping the DMSO concentration less than 5% (v/v). Extinction coefficients (A. M-1.cm-1) used were $1.1 \times 10^5$ at 280 nm for apo-hemopexin and for heme binding by both rabbit and human hemopexin after nitration in vitro $1.2 \times 10^5$ at 280 nm and $1.4 \times 10^5$ at 405 nm. Mesoheme (iron-mesoporphyrin IX) was used instead of protoheme (iron-protoporphyrin IX), due to its greater stability and meso-heme-hemopexin is chemically and biologically equivalent to protoheme-hemopexin (11).

Nitration by In Vitro Myeloperoxidase/Glucose Oxidase (MPO/GO) Treatment and Assessment of Heme Binding after Nitration Purified apo-hemopexin or heme-hemopexin complexes (10 μM) in 0.1 M sodium phosphate solution, pH 7.4, containing 2 mM NaCl were incubated with 53 nM myeloperoxidase, 2 nM glucose oxidase, 0.1 mM DTPA, and 50 μM sodium nitrite (NaNO) at 37° C. for up to 4 h (2, 3). This reaction mixture was kept on ice until the addition of, glucose (0.56 mM), the glucose oxidase substrate, generating $H_2O_2$. Myeloperoxidase utilizes $H_2O_2$ and $NO^{2-}$ as substrates to catalyze the nitration of amino acid residues (e.g. tyrosine) in proteins. During this incubation, aliquots of hemopexin (6 μl; 2.85 μg) were removed at the indicated times for immuno-blotting (250 ng) and for LC-MS/MS (3 μg) and denatured in Laemmli buffer. To more readily distinguish between the extents of nitration of apo- and heme-hemopexin by immunoblotting, these concentrations were reduced by 75%.

To assess heme binding of MPO/GO-treated apo-hemopexin, aliquots were taken at the times indicated from reaction mixtures after the addition of either glucose or an equal volume of water for the control incubation. To thoroughly remove glucose, the aliquots were immediately diluted 3-fold with ice-cold PBS (10 mM phosphate buffer pH 7.4, 150 mM NaCl) and concentrated in a centrifugal concentration and desalting filter unit with a 10 kDa cut-off, which is sold under the trade name Centricon (EMD Millipore, Billerica, Mass., USA) for 15 min at 4° C. (5000×g) such as is known in the art. This was repeated twice more to generate ~500 μl concentrated protein solution for heme binding analysis.

Nitrotyrosine Quantitation by Immunoblotting

The extent of nitration of the hemopexin samples was determined after electrophoresis (10% Tris HCl gels) by immuno-blotting after transfer to a sequencing membrane sold under the trade name Sequi-blot PVDF membrane (Bio-Rad Laboratories, Hercules, Calif., USA). Anti-3'nitrotyrosine rabbit polyclonal antibody (3 µg/ml; antigen-peroxynitrite-treated KLH, Cayman Chemical, Ann Arbor, Mich., USA) was used in combination with horseradish peroxidase conjugated goat anti-rabbit IgG (dilution 1:50,000). After stripping the blot was reprobed for total hemopexin (i.e., both native and nitrated hemopexin) by incubating with a goat anti-human HPX polyclonal primary antibody (raised by the inventor) at a 1:500 dilution with a rabbit anti-goat IgG secondary antibody (1:25,000 dilution). Signal was detected in both cases with an HRP western blotting substrate sold under the trade name Lumigen PS-3 Amigen (LUMIGEN, Southfield, Mich., USA) as substrate for the enhanced chemi-luminescence with an acridan-based chemiluminescent and chemifluorescent HRP substrate for Western blot detection using X-ray film or CCD- or laser-based imagers sold under the trade name ECL Plus (Thermo Fisher Scientific, Rockford, Ill., USA) and the blot was scanned on a variable mode laser scanner sold under the trade name Typhoon Imager (GE Healthcare Bio-Sciences, Pittsburgh, Pa., USA). Quantitation was carried out using gel digitizing software sold under the trade name UN-SCAN-IT (Silk Scientific, Orem, Utah, USA) such as is known in the art.

LC-MS/MS Quantitation of Digested Hemopexin and SEQUEST Searches to Identify Tyrosine Nitration After electrophoresis of hemopexin samples gels were rinsed twice with pure water before brief staining with a triphenylmethane dye commonly referred to as a Coomassie dye reagent for detection of protein bands in sodium dodecyl sulfate polyacrylamide gel electrophoresis (SDS-PAGE) and 2D gels sold under the trade name Imperial Stain (Thermo Fisher Scientific, Rockford, Ill., USA) and rapid de-staining, a gel fragment was excised vertically across the hemopexin band to ensure inclusion of the nitrated protein. After trypsin digestion (20 µg/ml in 50 mM ammonium bicarbonate) following standard procedures (3), the tryptic peptides were then used for characterization of oxidation sites using a MALDI-TOF mass spectrometer sold under the trade name AB Voyager DE Pro (AB SCIEX, Framingham, Mass., USA). Sampling was carried out with an Eksigent splitless binary nano-LC (Thermo Fisher Scientific, Rockford, Ill., USA), connected to a Thermo Finnigan LTQ linear ion trap (Thermo Fisher Scientific, Rockford, Ill., USA), equipped with a Proxeon nanospray source (Thermo Fisher Scientific, Rockford, Ill., USA) with data dependent scans. SEQUEST searches were performed using Xcalibur BioWorks 3.1 (Thermo Fisher Scientific, Rockford, Ill., USA) for the initial identification of low basal levels of nitration using human (gi 11321561), rabbit (gi 130500366), and rat (gi 123036) hemopexin sequences from the NCBI Proteins resource.

The relative quantitation of nitrated tyrosine sites was carried out using selective reaction monitoring (SRM) such as is known in the art. Synthetic peptides were synthesized by Celtek Peptides (Nashville, Tenn., USA) with the cysteines carbamidomethylated. The lyophilized samples of the synthetic peptides were diluted in pure water and standardized to the arginine curve determined with the 2,4,6-trinitrobenzenesulfonic acid method of Snyder & Sobocinski (12) as described below. SRM scans were done for the internal reference peptide, NFPSPVDAAFR (SEQ ID NO 10): 611.5, for the unmodified peptide YYCFQGNQFLR (SEQ ID NO 1): 748.5, and for the modified peptide, YY"CFQGNQFLR (SEQ ID NO 1): 771.6. The MS/MS chromatographic peak areas of the peptides NFPSPVDAAFR (SEQ ID NO 10) (mass range 959.2-960.4), YYCQGNQFLR (SEQ ID NO 1) (mass range 734.2-734.4) and YY"CFQGNQFLR (mass range 734.2-734.4) were quantitated using Xcalibur software (Vienna, Va., USA). The chromatographic peak area ratios were graphed versus time of exposure the nitrating in vitro treatment.

MASCOT Database Searches and Identification of COMs in ROS-Treated Apo-Hemopexin Rabbit apo-hemopexin (10 µM) in PBS was incubated for 15 min at 37° C. with HOCl (1:2.5, 1:10, 1:20), $H_2O_2$ (1:1, 1:2.5, 1:10), tBuOOH (1:1, 1:2.5, 1:10), or PBS alone as control as published (1). Proteolysis of samples and LC-MS/MS were conducted as described above. Searches of data in Thermo RAW files were set up using MASCOT Daemon (version 2.4.0; Matrix Science Inc, Boston, Mass., USA) and submitted to an in house MASCOT Server (version 2.4.1; Matrix Science Inc, Boston, Mass., USA). The rabbit hemopexin sequence (gi 130500366) from the NCBI Proteins resource was searched with "semi-Trypsin" selected as the proteolytic enzyme. The precursor mass tolerance was set at ±2 Da and the fragment mass tolerance was set at ±1 Da. MASCOT has the limitation of allowing only nine modifications per search. The database was searched as follows. The first pass search was for oxidation of Phe, His, Lys, Met, Arg, Trp, Tyr, and kynurenine and oxolactone modifications of Trp. The second pass search focused on di-oxidation of Phe, Lys, Met, Arg, Trp, and Tyr, tri-oxidation of Trp and Tyr, and modification of Trp to hydroxykynurenine. Samples treated with tBuOOH were additionally searched for t-butylation and di-t-butylation of Trp and Tyr. Samples treated with HOCl-treated were also searched for chlorination of Tyr, His, Lys, and Trp, di-chlorination of Trp and Tyr, and tri-chlorination of Trp and Tyr was included. Modifications were initially validated manually. Further verifications of COMs were carried out using Thermo Xcalibur Qual Browser (version 2.0.7; Thermo Fisher Scientific, Rockford, Ill., USA).

Results

Our analytical strategy was to: identify endogenous nitrated amino acids in hemopexin isolated from human, rabbit and rat plasma samples; identify their location in the primary amino acid sequence; determine the extent of conservation among the three species of hemopexin; determine their relative abundance; and, map them onto the 3D-crystal structure of hemopexin. We then planned to investigate in vitro if this nitration impaired biological functions of hemopexin such as heme binding. Finally, we wished to assess if the amino acids that are nitrated are also oxidatively modified by three ROS previously shown to potentially impair heme binding by hemopexin. We reasoned that, if so, then there are regions of the protein vulnerable to damage by RNS and ROS leading to loss of function of hemopexin in certain inflammatory conditions.

Figure 6:
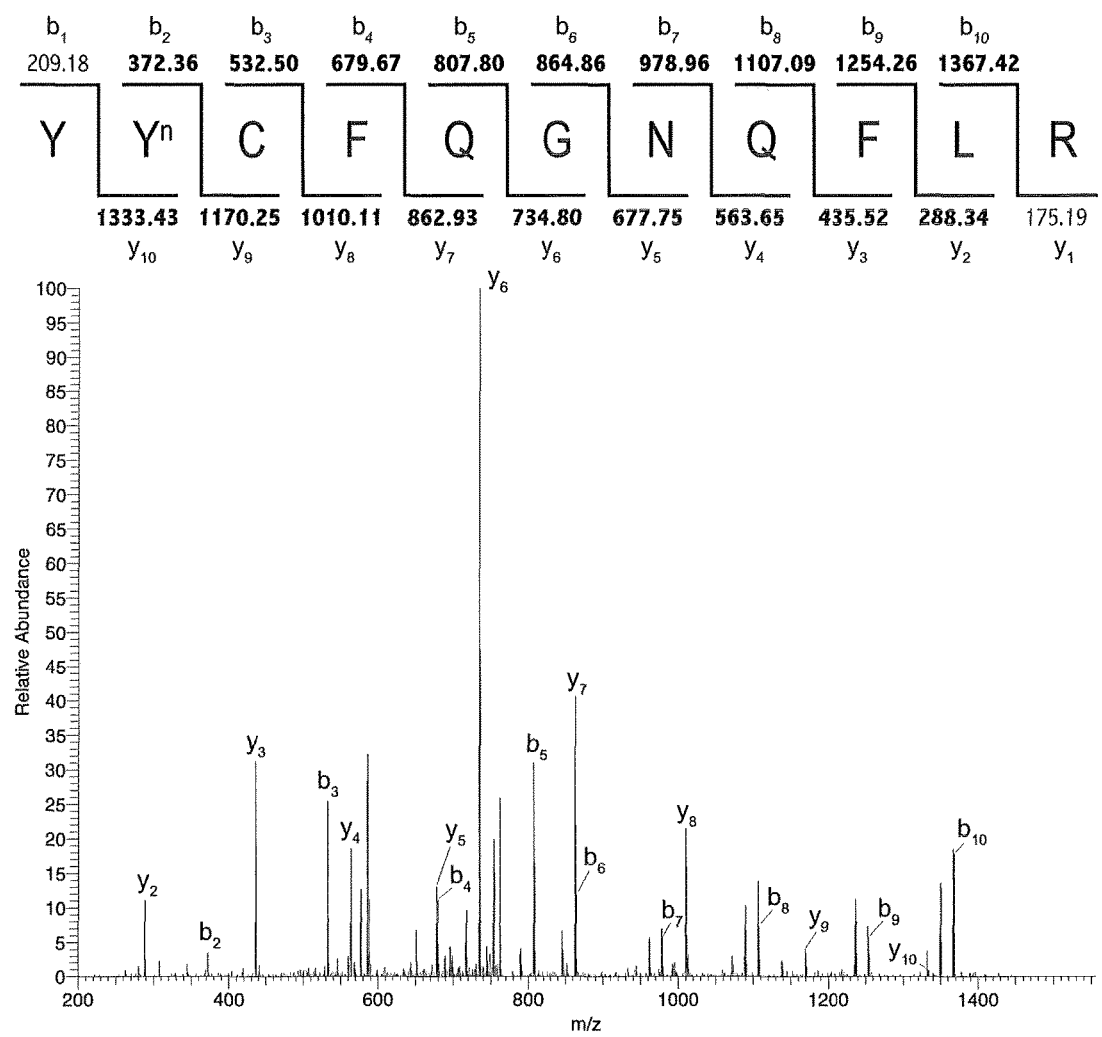
FIG. 6 is a spectrogram showing that nitration of rabbit hemopexin occurs in vivo at $Y_{201}$. Tyrosine nitration was detected by LC-MS/MS analysis of hemopexin isolated from rabbit plasma. MS/MS data analysis software sold under the trade name Xcalibur BioWorks (Thermo Fisher Scientific, Rockford, Ill., USA) was used to identify $Y''_{201}$ on the tryptic peptide YY"CFQGNQFLR (SEQ ID NO 1) (see Table I for XCorr value). Matched b and y ions are shown in bold in the ions diagram (above) and are indicated next to corresponding peaks in the MS/MS spectrum.
Figure 7:
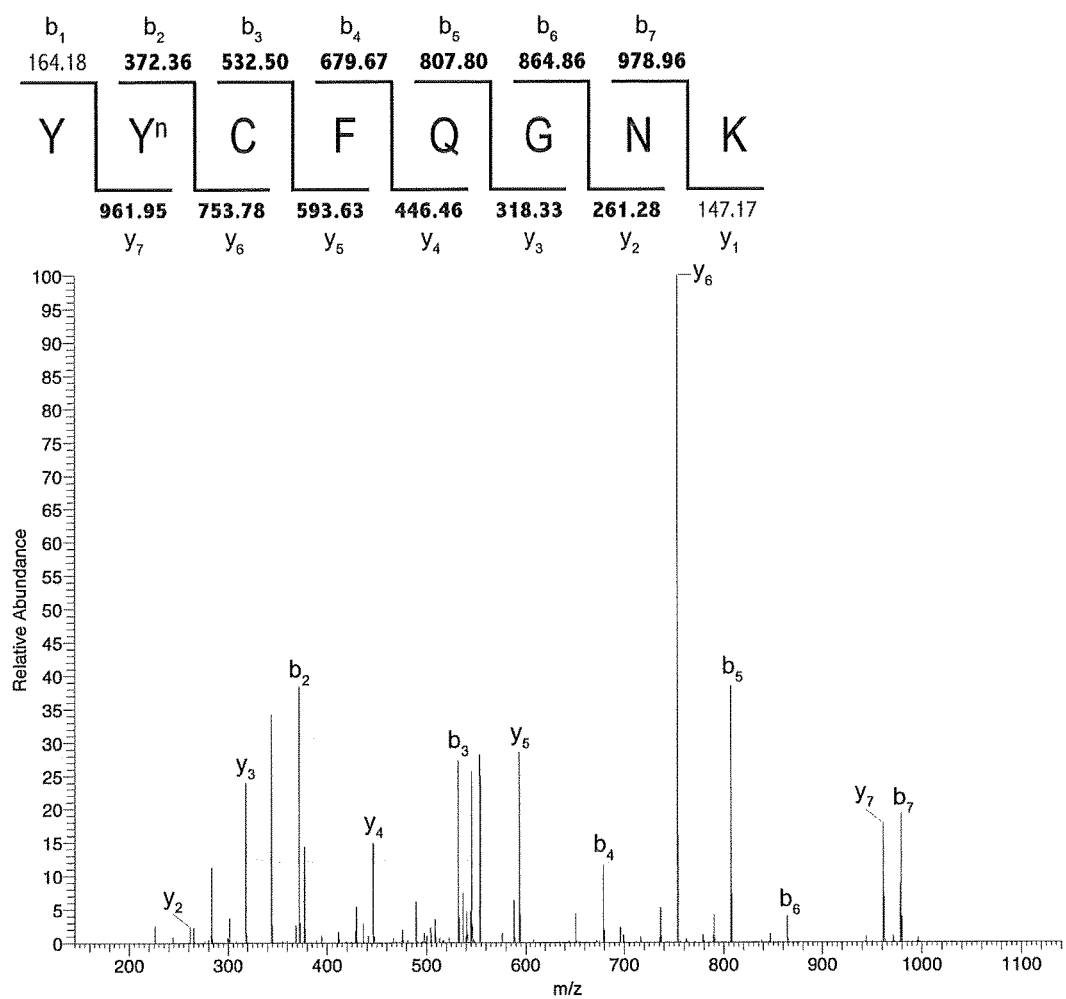
FIG. 7 is a spectrogram showing that nitration of rat hemopexin occurs in vivo at $Y_{118}$. Tyrosine nitration was detected by LC-MS/MS analysis of hemopexin isolated from rat plasma. Xcalibur BioWorks was used to identify $Y''_{118}$ on the tryptic peptide YY"CFQGNQFLR (SEQ ID NO 1) (see Table I for XCorr value). Matched b and y ions are shown in bold in the ions diagram (above) and are indicated next to corresponding peaks in the MS/MS spectrum.

Identification and Semi-Quantitation of Nitrated Tyrosine Residues in Human Hemopexin Using LC-MS/MS, which are Present Also in the Rat and Rabbit Congeners Consistent with nitration in vivo, LC-MS/MS data show that native isolates of hemopexin from plasma of human, rabbit and rat, which are highly conserved proteins (13), are nitrated at low abundance (see Table I; for human hemopexin MS/MS data see FIG. 1). Using the relative abundance (y axis of the MS/MS spectrum), the nitrotyrosine most often nitrated was tyrosine-199 ($Y_{199}$) in the conserved tryptic peptide YY″CFQGNQFLR (SEQ ID NO 1) from human hemopexin (FIG. 1). The same amino acid is nitrated in rabbit ($Y_{201}$) and rat ($Y_{118}$) hemopexin, respectively (see Table I; for rabbit and rat hemopexin MS/MS data see FIGS. 6 and 7, respectively). This amino acid numbering follows the precursor peptide sequences (derived from the gene) of human, rabbit and rat hemopexin from the NCBI Proteins resource. The COBALT multiple sequence alignment tool reveals that each molecule of human hemopexin has 16 tyrosine residues of which 13 are conserved with hemopexin from Norway rat and 15 with rabbit hemopexin, including $Y_{199}$ of human HPX. Mapping the human hemopexin sequence onto the rabbit 3-D crystal structure revealed that this tyrosine (labeled $Y''_{199}$ in FIG. 2A) interacts directly with the heme propionate in the D ring suggesting that heme binding is likely to be decreased or inactivated by this nitration. It is noted that $Y_{199}$ of human hemopexin is homologous to $Y_{176}$ in the published rabbit hemopexin crystal structure of the mature, secreted protein (14); the 25 amino acid difference being due to the signal peptide (using PDB 1QHU and rabbit hemopexin precursor sequence UniProtKB accession # P20058. Also, the sequence 216-SHRNSTQ-222 is missing from the 1QHU structure and the following histidine was inadvertently assigned $H_{222}$; consequently, from $H_{222}$ to the C-terminus the difference in numbering between the gene and the mature protein is only 24.) In the enlarged view of the heme binding site (FIG. 2B), $Y_{201}$ in the rabbit structure is near the surface of the apo-protein for heme binding; in contrast, $Y_{200}$ is far from the heme pointing away and buried deeply in the protein interior of the N-domain (FIG. 2B). In rabbit hemopexin, in addition to this conserved nitrated $Y_{201}$, four other endogenously nitrated tyrosines have been unambiguously identified in the MS/MS analyses of rabbit hemopexin isolates ($Y_{121}$, $Y_{229}$, $Y_{317}$, $Y_{325}$, Table I). $Y_{201}$ and $Y_{229}$ are close to heme in the heme binding site; $Y_{121}$ is near the N-terminus; and $Y_{317}$ and $Y_{325}$ are in the C-domain. (FIGS. 2B & C).

Because hemopexin is not exposed to nitrating reagents during isolation, these observations support that tyrosine nitration occurs in vivo, normally with very low abundance, and the variation observed, which we recognize is from a small preliminary set of plasma samples, reflects the situation in vivo. Significantly, key residues in the heme binding site of hemopexin that help stabilize and orient the heme are vulnerable to nitration in vivo.

Enzymatic Nitration of Human Hemopexin In Vitro Increases the Abundance of $Y''_{199}$ in a Population of Hemopexin Molecules Because hemopexin is likely to be exposed to nitric oxide and other nitrating species in inflammatory conditions that can also accompany hemolysis, we wanted to determine the abundance of site-specific nitrated tyrosines of human hemopexin. For this in vitro nitration we used a gentle, controlled myeloperoxidase/glucose oxidase (MPO/GO)-mediated enzymatic nitration system based on published methods (2). There is an approximately 5-fold increase in nitration of human apo-hemopexin after two hours incubation with MPO/GO, detected by immuno-blotting with anti-3' nitrotyrosine antibody (FIG. 3A, 3B). Similar results were found for rabbit hemopexin (data not shown). Tyrosine residue $Y_{199}$ in the tryptic peptide YY″CFQGNQFLR (SEQ ID NO 1) detected in native human hemopexin is also nitrated in vitro detected and identified by LC-MS/MS analyses of trypsin digests of hemopexin (FIG. 3 C-E). MASCOT with the site analysis feature did not distinguish between $Y_{198}$ and $Y_{199}$ in this peptide in some analyses of human hemopexin or in some samples of rabbit hemopexin (i.e. between $Y_{200}$ and $Y_{201}$). However, as mentioned above, our identification of Hu$Y_{199}$/Rbt$Y_{201}$ as the nitrated tyrosine in this sequence is bolstered by the clear difference in location and solvent accessibility of these two neighboring residues in the 3-D structure of hemopexin. Significantly, selective reaction monitoring (SRM) of human apo-hemopexin at various times after in vitro nitration shows that the extent of nitration of $Y_{199}$ in the YY″CFQGNQFLR (SEQ ID NO 1) peptide increases with the length of exposure time to MPO/GO (FIG. 3 C-E). Similar SRM data have also been obtained for the extent of nitration of $Y_{201}$ of rabbit hemopexin in vitro (data not shown).

Overall, these data reveal that nitration of human hemopexin increases with time and the abundance of nitration of $Y_{199}$, as a representative target, increases as nitration proceeds. This demonstrates that the population of hemopexin molecules with one or more nitrated tyrosines in the heme binding site may increase in biological fluids depending upon the duration of exposure to and the concentration of nitrating species.

Figure 2A:
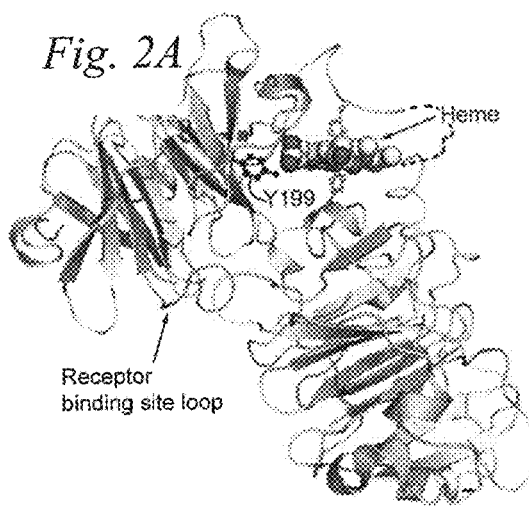
FIGS. 2A through 2C are ribbon diagrams of the crystal structure of rabbit HPX that illustrate the covalent oxidatively modified residues in a cluster of amino acids in the functionally important heme binding site. These structures were generated using PyMol (DeLano, W. L., the PyMOL Molecular Graphics System, version 1.3, provided by Schrodinger, LLC, New York, N.Y.).
Figure 2B:
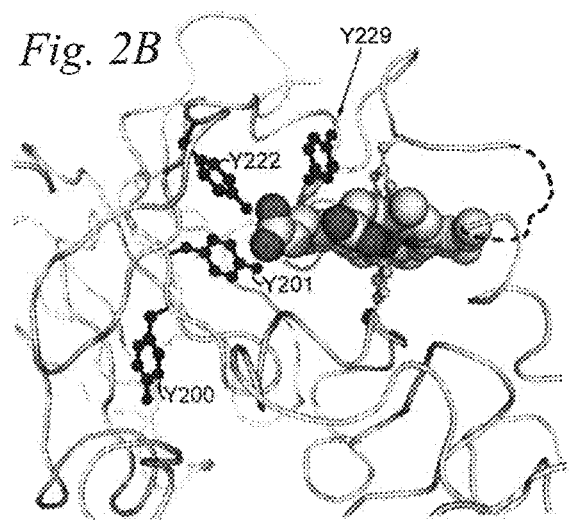
Figure 2C:
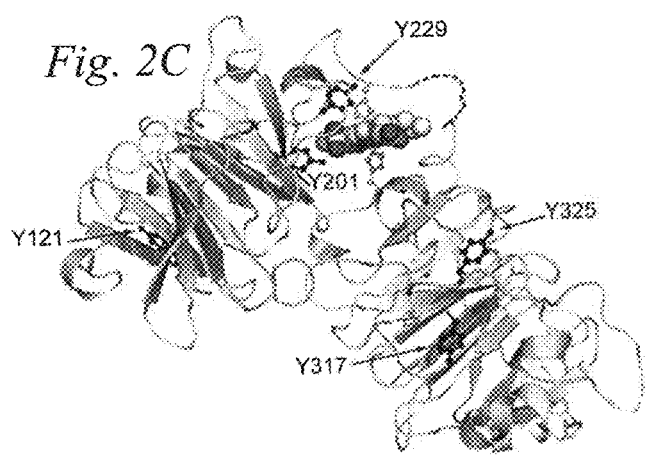

Apo-Hemopexin, the Circulating Form in Plasma, is More Susceptible to Nitration than the Heme-Hemopexin Complex As shown in FIGS. 2A-C, hemopexin is comprised of two β-propeller domains linked by a hinge region (14, 15). Heme binding causes several conformational changes in hemopexin: a compaction in size, enhanced inter-domain interactions and protection of the hinge region from proteolysis (15, 16). Therefore, we expected that apo-hemopexin, which normally predominates in human plasma and other biological fluids including CSF, would be more vulnerable to nitration than the heme-complex. The immuno-blot data in FIG. 4A show that nitrated human apo-hemopexin is more extensively nitrated than the heme-hemopexin complex (FIG. 4A). Significantly higher levels of nitration of apo-hemopexin are apparent within 10-15 minutes incubation with MPO/GO at 37° C. and continue to increase for 2 hours. Similar results have been obtained with rabbit hemopexin (data not shown).

Tyrosine Nitration Decreases the Ability of Human Hemopexin to Bind Heme

Using absorbance spectroscopy, heme binding by human hemopexin was impaired progressively during incubation with the MPO/GO-nitrating system at 37° C. (FIG. 4B), consistent with the location of $Y''_{166}$ and other nitrated tyrosines close to the bound heme. The extent of heme binding by hemopexin decreased as the time of incubation with MPO/GO increased from 15-150 min (FIG. 4B). Consequently, nitration in vivo is likely to decrease the ability of hemopexin to bind heme, thus inactivating this important protective function. A similar extent of nitration with decreases in heme binding was found for rabbit hemopexin (data not shown).

ROS Also Covalently Modify Apo-Hemopexin and Impair Heme Binding

We anticipated that nitrated tyrosine residues of hemopexin would also be susceptible to damage by ROS and, also, that by comparing results from several different conditions (i.e. type of ROS and ratio of hemopexin:ROS) a pattern showing a hierarchy of susceptible amino acids would become apparent by their COMs. The details of the peptides and their modified amino acids identified by LC-MS/MS in rabbit hemopexin are presented in Tables II and III. The extent and type of modification of 8 targeted amino acids is summarized in Table IV and FIG. 5. Several covalently oxidatively modified peptides were also identified using MASCOT, but at a lower level of confidence because the amino acid was not unambiguously identified (Table III). Although exposure of apo-hemopexin to high, supra-physiological, molar ratios of $H_2O_2$ impairs heme binding (1), no amino acid modifications were unambiguously identified by MASCOT searches in hemopexin exposed to $H_2O_2$ at 1:1, 1:2.5 or 1:10 molar ratios.

Figure 5B:
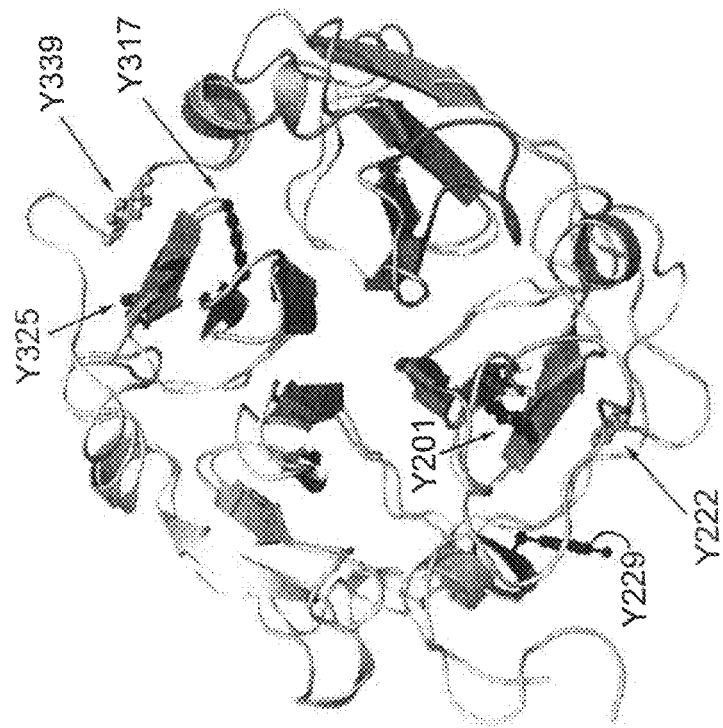
FIGS. 5A and 5B show two ribbon diagrams of the crystal structures of HPX when it is exposed to RNS and ROS and the distribution of covalently oxidatively modified amino acids after the exposure. ROS-modified residues are from rabbit hemopexin treated with HOCl or tert-butyl hydroperoxide (see also Table II, below).
Figure 5A:
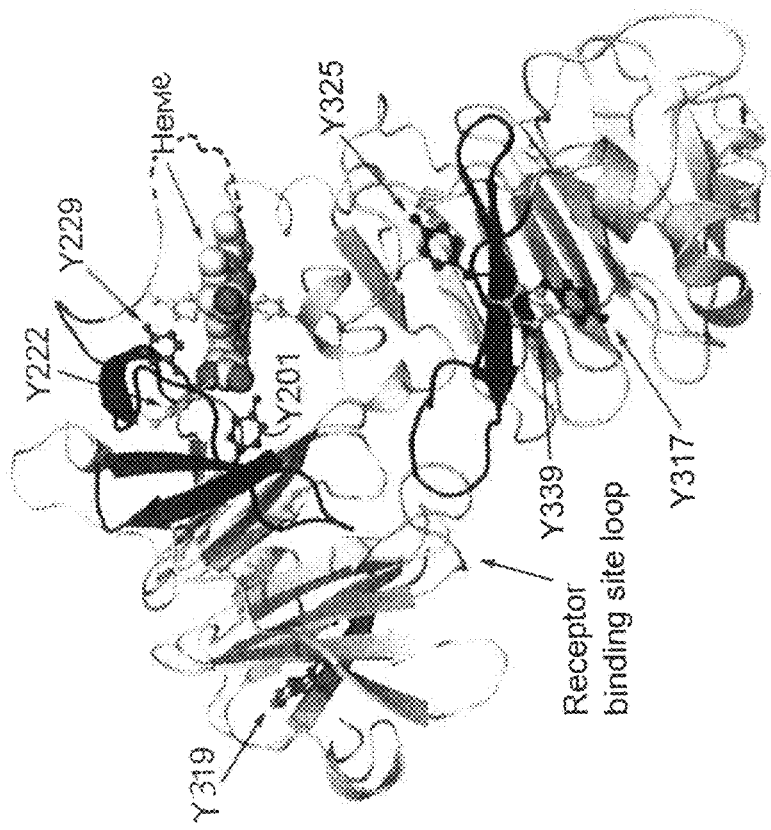

As summarized in FIG. 5A, both $W_{119}$ and $Y_{121}$ have single modifications and are located in peptide VWVYT-SEK (SEQ ID NO 7) at the N-terminus. $W_{119}$ is oxidized by HOCl (1:10) and $Y_{121}$ is endogenously nitrated. The six remaining tyrosines of which four were endogenously nitrated, fall into two groups of three. Those in the heme binding sites sustained more than one COM, whereas those in the C-domain only had one COM. $Y_{201}$ and $Y_{229}$ that were nitrated endogenously were also modified after rabbit hemopexin was incubated with tert-butyl hydroperoxide (tBuOOH); in addition $Y_{229}$ modified by hypochlorous acid (HOCl). $Y_{222}$ was susceptible to HOCl and to tBuOOH. In the C-domain of hemopexin, $Y_{317}$ and $Y_{325}$ were nitrated and $Y_{339}$ was chlorinated by HOCl (1:10). The six peptides containing these modified amino acids form two contiguous regions: one on each domain ($Y_{200}$ to $R_{236}$ and $L_{316}$ to $K_{341}$). When the residues that are reactive are mapped onto the heme-hemopexin crystal structure they are not solvent accessible (FIG. 5B), pointing again to the large conformation change driven by heme binding that compacts the protein (17). The N- and C-domains of hemopexin are highly homologous four-bladed β-propellors (13). When these domain structures are superimposed (N- to C-orientation), the three endogenously nitrated tyrosines in the N-domain reside in a different HPX repeat from the three in the C-domain (FIG. 5C).

DISCUSSION

As recently reviewed (18), several of the diseases in which hemopexin plasma levels increase are associated with inflammation, increased activity of nitric oxide synthase and oxidative stress. Thus, hemopexin is expected to be exposed to high levels of oxidative species. Because proteins can be inactivated by oxidative modifications from exposure to RNS and ROS, we reasoned that the increased levels of hemopexin might be a response to damage in which case protein levels per se would not necessarily reflect the extent to which hemopexin is functional, i.e. capable of binding to heme or its receptors, thus limiting its chemical reactivity or ability to clear heme from the circulation, respectively. In proteins, generally, histidine, lysine, cysteine and methionine residues are oxidized, whereas tyrosine is nitrated. The most common and stable oxidation product of proteins generates the carbonyl derivative of lysine, threonine, arginine and proline; and carbonylated hemopexin had been detected in plasma from patients with Alzheimer's Disease [AD, (19)]. In fact, hemopexin was proposed to be a marker of this disease (19); but carbonylation was not shown to compromise the biological function of hemopexin. In contrast here, we have identified key amino acid residues on hemopexin that are particular targets for oxidative damage by RNS and ROS and show that they reside in the heme-binding site. Consequently, heme binding is impaired, which is an important means whereby hemopexin protects all cells from heme toxicity including the brain neurons and other brain cells (20).

The data presented here show that native human, rabbit and rat hemopexin are nitrated endogenously (i.e. in vivo) and, significantly, the prevalent nitrotyrosine identified, $Y''_{199}$ in the human sequence, is conserved in these three species of hemopexin and interacts directly with the heme ligand. The natural low abundance of $Y''_{199}$ shows that the majority of hemopexin molecules in human plasma are normally not nitrated. Consistent with this location in the heme site, incubation of hemopexin with an enzymatic nitrating system (MPO/GO) in vitro significantly decreased heme binding, which was progressive as nitration proceeded. Additional in vitro studies showing that the longer the exposure of human hemopexin to nitrating species the greater the relative increase in the abundance of $Y''_{199}$ in a population of hemopexin molecules. Overall, these data bolster our hypothesis that nitration reflects specific events in vivo and that if hemopexin encounters RNS at sufficient concentration in biological fluids, like plasma and CSF, it could be damaged by nitration of tyrosines in the heme binding site and lose its ability to bind heme. Importantly, these studies with human hemopexin were confirmed by similar analyses using rabbit hemopexin.

The identification of the nitrated tyrosine in the peptide YY″CFQGNQFLR (SEQ ID NO 1) as $Y''_{201}$ in rabbit hemopexin, rather than the N-terminal $Y_{200}$ is supported not only by several MASCOT analyses but also inspection of the hemopexin 3-D structure, which reveals that $Y_{200}$ is buried deeply in the N-domain away from the heme binding site, and is also not close to the proposed heme docking site at the end of the tunnel in the N-domain (13). There is little, if any, flexibility in this region because each hemopexin domain is a very stable protein structure; this is intrinsic to the four-bladed propellers constrained in part by several di-sulfide bonds as well as by the ions in the central tunnel that coordinate with the carbonyl and amino groups of the peptide backbone (14).

We also wanted to determine if the damage to hemopexin by, albeit high, supraphysiological levels of, $H_2O_2$ and HOCl previously shown by us to impair heme binding by ~30-40% (1) also modified the tyrosine residues that were nitrated and, furthermore, if there were other oxidant-susceptible amino acid residues in different regions of the protein. Using MASCOT, eight amino acids were identified with covalent oxidative modifications. Our principle findings show that five tyrosines were endogenously nitrated, the same three $Y_{201}$, $Y_{222}$ and $Y_{229}$ in the heme binding site and another in the C-domain, together with a tryptophan residue in the N-terminus were covalently modified by ROS including t-BuOOH. The three tyrosines in the heme binding site sustained more than one COM, two with 3-4 COMs, whereas the three tyrosines in the C-domain only had one COM. The N-terminus of rabbit hemopexin was another vulnerable region where $W_{119}$ and $Y_{121}$ are located. In human, these two N terminal residues may be protected from oxidation because there is an O-linked oligosaccharide chain attached to the N-terminal threonine of human hemopexin (21) that is not present in the rabbit protein.

The clustering of modified amino acids with the greatest number and variety of modifications in the heme binding site is clear and quite remarkable given the different chemical reactivity of the RNS and ROS employed. Ligand binding often protects the key amino acids involved in the interaction and this seems to be the case with hemopexin. Heme binding protects the heme-iron coordinating histidine residues from chemical modification (22). Thus, apo-hemopexin, the predominant form normally present in biological fluids appears potentially vulnerable to inactivation. The modified amino acids identified constitute a hierarchy susceptible to damage, none of which are close to the region implicated in receptor recognition (17), or in the proposed heme docking site at the wide end of the tunnel of the N-domain (13). The lack of detectable modifications of amino acids upon exposure to $H_2O_2$ was unexpected (a ratio of 1:10 hemopexin: $H_2O_2$ reduced binding by ~30% (1). This may be due to the fact that in the absence of reduced metals (ferrous and cuprous ions) $H_2O_2$ is a relatively weak oxidizing agent (23); or alternatively, the carbohydrate chains may be altered by $H_2O_2$ as shown for haptoglobin (24). Nevertheless, hemopexin does not have to be glycosylated to bind heme (14).

We draw several conclusions from these observations: First, we have identified in hemopexin a hierarchy of eight amino acids that are targeted by RNS and physiologically-relevant ROS and three of these particularly vulnerable tyrosines cluster in the heme binding site of hemopexin. Second, the nitration of human hemopexin can diminish its ability to bind heme and the proportion of nitrotyrosines, especially of $Y_{199}$ that interacts directly with heme, increases with extent of exposure to nitrating conditions in vitro. This supports that the protective heme binding by hemopexin may be decreased by nitration in pathological states. Third, the large conformational change that hemopexin undergoes driven by heme binding protects the vulnerable tyrosine residues in the heme binding site from damage; consistent with this, the heme-hemopexin complex is essentially stable in the presence of MPO/GO nitration and ROS (1) emphasizing the paramount importance of the extracellular anti-oxidant role of hemopexin.

Proteins are oxidized and nitrated in oxidative stress when activated neutrophils produce their defensive "respiratory burst" generating superoxide, which reacts with nitric oxide (NO.) forming peroxy nitrate (ONOO—); and, also by peroxidase activity in the presence of $NO^{2-}$ and hydrogen peroxide (25). NO. is produced by four members of nitric oxide synthase (NOS): neuronal, endothelial (e), inducible (i) and mitochondrial. eNOS is present in cells that line all blood vessels and NO. causes vasodilation. Following immunological or inflammatory stimuli, macrophages and brain astrocytes produce NO. at high levels for hours or days. Hemopexin helps restrain systemic inflammatory responses in part by sequestering heme from immune cells to prevent heme-mediated activation of TLR4 (26) with release of inflammatory cytokines (27-29); to prevent toxic effects of heme (30); and to safely transport heme to tissues (11, 20). These COMs of hemopexin that we have identified may represent attacks on hemopexin in niches of the body where there is inflammation and oxidative stress with activated endothelial and immune system cells including neutrophils and astrocytes that generate a variety of RNS and ROS. Hemopexin structure is protected by the extensive di-sulfide bonds and lack of free sulfhydryl groups, which confers stability to the protein in an oxidizing environment. Another mitigating factor protecting apo-hemopexin in vivo is that in biological fluids including plasma and CSF there are abundant preferential protein targets such as albumin (1). In fact, in plasma albumin is present at approximately 80-fold molar excess over hemopexin.

One condition where we expect that the extent of hemopexin nitration in vivo will increase as inflammation progresses is in sepsis; and tyrosine nitration of proteins has been documented in sepsis (31, 32). Hemopexin deficiency states develop in clinical sepsis and are associated with high morbidity; and in mice models of severe sepsis hemopexin supplementation is life-saving (33). We speculate that if the oxidatively modified hemopexin is recognized as a non-native protein, it would be targeted to the lysosomes for catabolism, rather than the recycling endosomes, thus contributing to the development of hemopexin deficiency states documented in sepsis.

Hemopexin acts during inflammation that accompanies ischemic (20) and hemorrhagic (34) stroke by diminishing heme's chemical activity (30) and by delivering it safely to cells. We anticipate that hemopexin may be inactivated in the cerebral spinal fluid (CSF) in Alzheimer's disease (AD), the neurodegeneration of which has been linked to oxidative stress and reactive nitrogen species (35). In fact, increased levels of nitrated proteins have been detected in brain tissue and CSF of AD subjects (35). Hemopexin levels are elevated in CSF in inflammation (36) and in AD subjects compared with age-matched controls (7). While this may be due to its known induction by interleukin-6 (13), hemopexin may be inactivated because increased levels of 3-nitrotyrosine have been detected in the inferior parietal lobe and hippocampus in mild cognitive impairment (MCI) (37). Such nitrosative damage occurs early in course of MCI and protein nitration was proposed to be important for conversion from MCI to AD.

Overall, our data establish a strong foundation for analyzing hemopexin to determine its potential as a biomarker for conditions of oxidative stress in which nitration has been detected including neurodegeneration (e.g. MCI and AD), systemic inflammatory responses (e.g. acute lung injury, SCD, sepsis, shock and multiple organ failure syndrome) and heme toxicity during hemolysis. The type and extent of nitration will reflect biological processes and, together with other oxidative modifications, COMs of hemopexin may provide a more specific biomarker of certain disease states, than hemopexin levels alone. Using the amounts of functional hemopexin to assess the extent of heme toxicity and the timing of hemopexin replenishment therapy in hemopexin deficiency states, will provide physicians with evidence-based therapies in conditions like sepsis, which are currently lacking.

BIBLIOGRAPHY

1. P. Hahl, T. Davis, C. Washburn, J. T. Rogers, A. Smith, Mechanisms of neuroprotection by hemopexin: modeling the control of heme and iron homeostasis in brain neurons in inflammatory states. *Journal of Neurochemistry* 125, 89 (Jan. 25, 2013).
2. V. A. Kostyuk, T. Kraemer, H. Sies, T. Schewe, Myeloperoxidase/nitrite-mediated lipid peroxidation of low-density lipoprotein as modulated by flavonoids. *FEBS Letters* 537, 146 (Feb. 27, 2003).
3. B. B. Willard, C. I. Ruse, J. A. Keightley, M. Bond, M. Kinter, Site-specific quantitation of protein nitration using liquid chromatography/tandem mass spectrometry. *Analytical Chemistry* 75, 2370 (May 15, 2003).
4. H. Ischiropoulos, Protein tyrosine nitration—an update. *Arch Biochem Biophys* 484, 117 (Apr. 15, 2009).
5. H. Ischiropoulos, Biological selectivity and functional aspects of protein tyrosine nitration. *Biochem Biophys Res Commun* 305, 776 (Jun. 6, 2003).
6. R. Zhang et al., Systemic immune system alterations in early stages of Alzheimer's disease. *Journal of neuroimmunology* 256, 38 (Mar. 15, 2013).
7. E. M. Castano, A. E. Roher, C. L. Esh, T. A. Kokjohn, T. Beach, Comparative proteomics of cerebrospinal fluid in neuropathologically-confirmed Alzheimer's disease and non-demented elderly subjects. *Neurol. Res.* 28, 155 (March, 2006).

8. J. D. Eskew, R. M. Vanacore, L. Sung, P. J. Morales, A. Smith, Cellular protection mechanisms against extracellular heme: heme-hemopexin, but not free heme, activates the N-terminal c-Jun kinase. *J. Biol. Chem.* 274, 638 (1999).
9. W. T. Morgan et al., Identification of the histidine residues of hemopexin that coordinate with heme-iron and of a receptor-binding region. *J. Biol. Chem.* 268, 6256 (1993).
10. P. Vretblad, R. Hjorth, The use of wheat-germ lectin-Sepharose for the purification of human haemopexin. *Biochem. J.* 167, 759 (1977).
11. A. Smith, W. T. Morgan, Haem transport to the liver by haemopexin. Receptor-mediated uptake with recycling of the protein. *Biochem. J.* 182, 47 (1979).
12. S. L. Snyder, P. Z. Sobocinski, An improved 2,4,6-trinitrobenzenesulfonic acid method for the determination of amines. *Anal Biochem* 64, 284 (March, 1975).
13. A. Smith, in *Handbook of Porphyrin Science. Biochemistry of Tetrapyrroles*, K. M. Kadish, K. M. Smith, R. Guilard, Eds. (World Scientific Publishing Co. Pte. Ltd., Singapore, 2011), vol. 15, pp. 217-356.
14. M. Paoli et al., Crystal structure of hemopexin reveals a novel high-affinity heme site formed between two beta-propeller domains. *Nature Struct. Biol.* 6, 926 (1999).
15. W. T. Morgan, A. Smith, Domain structure of rabbit hemopexin. Isolation and characterization of a heme-binding glycopeptide. *J. Biol. Chem.* 259, 12001 (1984).
16. A. Smith, W. T. Morgan, in *Protides of the Biological Fluids*, H. Peeters, Ed. (Pergamon Press, Oxford, England, 1984), vol. 31, pp. 219-224.
17. W. T. Morgan et al., Use of hemopexin domains and monoclonal antibodies to hemopexin to probe the molecular determinants of hemopexin-mediated heme transport. *J. Biol. Chem.* 263, 8220 (1988).
18. A. Smith, in *Handbook of Porphyrin Science*, G. Ferreira, Ed. (World Publishing Co., 2013), vol. in preparation.
19. H. L. Yu, H. M. Chertkow, H. Bergman, H. M. Schipper, Aberrant profiles of native and oxidized glycoproteins in Alzheimer plasma. *Proteomics* 3, 2240 (November, 2003).
20. R. C. Li et al., Heme-hemopexin complex attenuates neuronal cell death and stroke damage. *J. Cereb. Blood Flow Metab.* 29, 953 (May, 2009).
21. N. Takahashi, Y. Takahashi, F. W. Putnam, Structure of human hemopexin: O-glycosyl and N-glycosyl sites and unusual clustering of tryptophan residues. *Proc. Natl. Acad. Sci., USA* 81, 2021 (1984).
22. W. T. Morgan, U. Muller-Eberhard, Chemical modification of histidine residues of rabbit hemopexin. *Arch. Biochem. Biophys.* 176, 431 (1976).
23. R. Stocker, J. F. Keaney, Jr., Role of oxidative modifications in atherosclerosis. *Physiological Reviews* 84, 1381 (October, 2004).
24. F. Vallelian et al., The reaction of hydrogen peroxide with hemoglobin induces extensive alpha-globin cross-linking and impairs the interaction of hemoglobin with endogenous scavenger pathways. *Free Radic. Biol. Med.* 45, 1150 (Oct. 15, 2008).
25. R. Radi, Nitric oxide, oxidants, and protein tyrosine nitration. *Proc Natl Acad Sci USA* 101, 4003 (Mar. 23, 2004).
26. J. D. Belcher et al., Heme triggers TLR4 signaling leading to endothelial cell activation and vaso-occlusion in murine sickle cell disease. *Blood* revised manuscript submitted, (2013).
27. X. Liang et al., Hemopexin down-regulates LPS-induced proinflammatory cytokines from macrophages. *J. Leukoc. Biol.* 86, 229 (Apr. 24, 2009).
28. T. Lin et al., Synergistic inflammation is induced by blood degradation products with microbial Toll-like receptor agonists and is blocked by hemopexin. *J Infect Dis* 202, 624 (Aug. 15, 2010).
29. T. Lin et al., Identification of Hemopexin as an Anti-Inflammatory Factor That Inhibits Synergy of Hemoglobin with HMGB1 in Sterile and Infectious Inflammation. *J Immunol* 189, 2017 (Aug. 15, 2012).
30. J. M. Gutteridge, A. Smith, Antioxidant protection by haemopexin of haem-stimulated lipid peroxidation. *Biochem. J.* 256, 861 (1988).
31. S. Lanone et al., Inducible nitric oxide synthase (NOS2) expressed in septic patients is nitrated on selected tyrosine residues: implications for enzymic activity. *Biochem J* 366, 399 (Sep. 1, 2002).
32. S. Chatterjee et al., Site-specific carboxypeptidase B1 tyrosine nitration and pathophysiological implications following its physical association with nitric oxide synthase-3 in experimental sepsis. *J Immunol* 183, 4055 (Sep. 15, 2009).
33. R. Larsen et al., A central role for free heme in the pathogenesis of severe sepsis. *Sci. Transl. Med.* 2, 51ra71 (Sep. 29, 2010).
34. L. Chen, X. Zhang, J. Chen-Roetling, R. F. Regan, Increased striatal injury and behavioral deficits after intracerebral hemorrhage in hemopexin knockout mice. *J. Neurosurg.* 114, 1159 (Dec. 3, 2010).
35. A. Castegna et al., Proteomic identification of nitrated proteins in Alzheimer's disease brain. *J Neurochem* 85, 1394 (June, 2003).
36. L. Saso et al., Differential changes in alpha2-macroglobulin and hemopexin in brain and liver in response to acute inflammation. *Biochemistry* (Mosc) 64, 839 (1999).
37. D. A. Butterfield et al., Elevated levels of 3-nitrotyrosine in brain from subjects with amnestic mild cognitive impairment: implications for the role of nitration in the progression of Alzheimer's disease. *Brain Research* 1148, 243 (May 7, 2007).
38. B. B. Willard, C. I. Ruse, J. A. Keightley, M. Bond, M. Kinter, Site-specific quantitation of protein nitration using liquid chromatography/tandem mass spectrometry. *Anal Chem* 75, 2370 (May 15, 2003).
39. N. Shipulina, A. Smith, W. T. Morgan, Heme binding by hemopexin: evidence for multiple modes of binding and functional implications. *J. Protein Chem.* 19, 239 (2000).

All references cited herein, including but not limited to published and unpublished applications, patents, and literature references, and also including but not limited to the references listed in the Appendix, are incorporated herein by reference in their entirety and are hereby made a part of this specification. To the extent publications and patents or patent applications incorporated by reference contradict the disclosure contained in the specification, the specification is intended to supersede and additionally or alternatively take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention. It is to be understood that while certain forms of the present invention have been illustrated and described herein, it is not to be limited to the specific forms or arrangement of parts described and shown.

What is claimed and desired to be secured by Letters Patent is as follows:

1. A method of detecting and measuring nitrated hemopexin and total hemopexin in a sample chosen from the group consisting of blood, plasma, serum, lung aspirate and cerebral spinal fluid of a subject chosen from the group consisting of humans, rabbits, and rats, the method comprising:
    a) performing an ELISA assay to each of total hemopexin and nitrated hemopexin in the sample and to controls to obtain test results;
    b) comparing the test results; and
    c) determining if an amount of nitrated hemopexin in the sample is elevated relative to an amount of the total hemopexin in the sample.
2. The method according to claim 1, wherein:
    a) the ELISA uses antibodies that detect total hemopexin and antibodies that detect nitrated hemopexin.
3. The method according to claim 2, wherein:
    a) the antibodies that detect nitrated hemopexin are a protein that has been generated by immunizing with an antigen selected from the group consisting of peptides having the following amino acid sequence, YY"CFQGNQFLR (SEQ ID NO 1), VWVY"TSEK (SEQ ID NO 2); DY"FLSCPGR (SEQ ID NO 5); LY"LIQDTK (SEQ ID NO 6); and (SEQ ID NO 7).

4. The method according to claim 3, wherein:
   a) the antigen is denatured so as to detect non-contiguous epitopes.

5. A method of detecting and measuring nitrated hemopexin and total hemopexin in a sample chosen from the group consisting of blood, plasma, serum, and cerebral spinal fluid of a subject chosen from the group consisting of humans, rabbits, and rats, the method comprising:
   a) performing an assay on the sample and controls to detect total hemopexin and nitrated hemopexin so as to obtain test results, wherein the assay is one of a western immuno-blot, an LC-MS/MS assay and a multi-plexing assay;
   b) comparing the test results of the sample and controls; and
   c) determining if an amount of nitrated hemopexin in the sample is elevated relative to an amount of the total hemopexin in the sample.

6. The method according to claim 5, wherein:
   a) the assay detects non-contiguous epitopes of hemopexin and nitrated hemopexin.

7. A method of detecting and measuring nitrated hemopexin and total hemopexin in a sample chosen from the group consisting of blood, plasma, serum, and cerebral spinal fluid of a subject chosen from the group consisting of humans, rabbits, and rats, the method comprising:
   a) performing an assay on the sample and controls to detect total hemopexin and nitrated hemopexin so as to obtain test results, wherein the assay is one of a western immuno-blot, an LC-MS/MS assay, a multi-plexing assay and an ELISA assay;
   b) comparing the test results of the sample and controls; and
   c) determining if an amount of nitrated hemopexin in the sample is elevated relative to an amount of the total hemopexin in the sample.

8. The method according to claim 3 wherein the amino acid sequence is YY"CFQGNQFL (SEQ ID NO 1).

9. The method according to claim 1 wherein the subject is human and the sample is blood.

* * * * *

```
                           SEQUENCE LISTING

<160> NUMBER OF SEQ ID NOS: 19

<210> SEQ ID NO 1
<211> LENGTH: 11
<212> TYPE: PRT
<213> ORGANISM: Homo sapiens

<400> SEQUENCE: 1

Tyr Tyr Cys Phe Gln Gly Asn Gln Phe Leu Arg
1               5                   10

<210> SEQ ID NO 2
<211> LENGTH: 8
<212> TYPE: PRT
<213> ORGANISM: Oryctolagus cuniculus

<400> SEQUENCE: 2

Val Trp Val Tyr Thr Ser Glu Lys
1               5

<210> SEQ ID NO 3
<211> LENGTH: 11
<212> TYPE: PRT
<213> ORGANISM: Oryctolagus cuniculus

<400> SEQUENCE: 3

Tyr Tyr Cys Phe Gln Gly Asn Gln Phe Leu Arg
1               5                   10

<210> SEQ ID NO 4
<211> LENGTH: 17
<212> TYPE: PRT
<213> ORGANISM: Oryctolagus cuniculus

<400> SEQUENCE: 4

Phe Asn Pro Val Ser Gly Glu Val Pro Pro Gly Tyr Pro Leu Asp Val
1               5                   10                  15

Arg

<210> SEQ ID NO 5
<211> LENGTH: 9
<212> TYPE: PRT
<213> ORGANISM: Oryctolagus cuniculus

<400> SEQUENCE: 5

Asp Tyr Phe Leu Ser Cys Pro Gly Arg
1               5

<210> SEQ ID NO 6
<211> LENGTH: 8
<212> TYPE: PRT
<213> ORGANISM: Oryctolagus cuniculus
```

```
<400> SEQUENCE: 6

Leu Tyr Leu Ile Gln Asp Thr Lys
1               5

<210> SEQ ID NO 7
<211> LENGTH: 7
<212> TYPE: PRT
<213> ORGANISM: Oryctolagus cuniculus

<400> SEQUENCE: 7

Val Tyr Val Phe Leu Thr Lys
1               5

<210> SEQ ID NO 8
<211> LENGTH: 11
<212> TYPE: PRT
<213> ORGANISM: Oryctolagus cuniculus

<400> SEQUENCE: 8

Gly Gly Tyr Thr Leu Val Asn Gly Tyr Pro Lys
1               5                   10

<210> SEQ ID NO 9
<211> LENGTH: 8
<212> TYPE: PRT
<213> ORGANISM: Rattus norvegicus

<400> SEQUENCE: 9

Tyr Tyr Cys Phe Gln Gly Asn Lys
1               5

<210> SEQ ID NO 10
<211> LENGTH: 11
<212> TYPE: PRT
<213> ORGANISM: Artificial sequence
<220> FEATURE:
<223> OTHER INFORMATION: Synthetic

<400> SEQUENCE: 10

Asn Phe Pro Ser Pro Val Asp Ala Ala Phe Arg
1               5                   10

<210> SEQ ID NO 11
<211> LENGTH: 36
<212> TYPE: PRT
<213> ORGANISM: Oryctolagus cuniculus

<400> SEQUENCE: 11

Val Trp Val Tyr Thr Ser Glu Lys Phe Asn Pro Val Ser Gly Glu Val
1               5                   10                  15

Pro Pro Gly Tyr Pro Leu Asp Val Arg Gly Gly Tyr Thr Leu Val Asn
            20                  25                  30

Gly Tyr Pro Lys
            35

<210> SEQ ID NO 12
<211> LENGTH: 36
<212> TYPE: PRT
<213> ORGANISM: Oryctolagus cuniculus

<400> SEQUENCE: 12

Val Trp Val Tyr Thr Ser Glu Lys Phe Asn Pro Val Ser Gly Glu Val
1               5                   10                  15
```

```
Pro Pro Gly Tyr Pro Leu Asp Val Arg Gly Tyr Thr Leu Val Asn
            20                  25                  30
Gly Tyr Pro Lys
        35

<210> SEQ ID NO 13
<211> LENGTH: 75
<212> TYPE: PRT
<213> ORGANISM: Oryctolagus cuniculus

<400> SEQUENCE: 13

Leu Asp Val Arg Asp Tyr Phe Leu Ser Cys Pro Gly Arg Gly His Arg
1               5                   10                  15

Ser Ser His Arg Asn Ser Thr Gln His Gly His Glu Ser Thr Arg Cys
            20                  25                  30

Asp Pro Asp Leu Val Leu Ser Ala Met Val Ser Asp Asn His Gly Ala
        35                  40                  45

Thr Tyr Val Phe Ser Gly Ser His Tyr Trp Arg Leu Asp Thr Asn Arg
    50                  55                  60

Asp Gly Trp His Ser Trp Pro Ile Ala His Gln
65                  70                  75

<210> SEQ ID NO 14
<211> LENGTH: 79
<212> TYPE: PRT
<213> ORGANISM: Homo sapiens

<400> SEQUENCE: 14

Arg Asp Val Arg Asp Tyr Phe Met Pro Cys Pro Gly Arg Gly His Gly
1               5                   10                  15

His Arg Asn Gly Thr Gly His Gly Asn Ser Thr His His Gly Pro Glu
            20                  25                  30

Tyr Met Arg Cys Ser Pro His Leu Val Leu Ser Ala Leu Thr Ser Asp
        35                  40                  45

Asn His Gly Ala Thr Tyr Ala Phe Ser Gly Thr His Tyr Trp Arg Leu
    50                  55                  60

Asp Thr Ser Arg Asp Gly Trp His Ser Trp Pro Ile Ala His Gln
65                  70                  75

<210> SEQ ID NO 15
<211> LENGTH: 78
<212> TYPE: PRT
<213> ORGANISM: Rattus norvegicus

<400> SEQUENCE: 15

Leu Asp Ala Arg Asp Tyr Phe Ile Ser Cys Pro Gly Arg Gly His Gly
1               5                   10                  15

Lys Leu Arg Asn Gly Thr Ala His Gly Asn Ser Thr His Pro Met His
            20                  25                  30

Ser Arg Cys Asn Ala Asp Pro Gly Leu Ser Ala Leu Leu Ser Asp His
        35                  40                  45

Arg Gly Ala Thr Tyr Ala Phe Ser Gly Ser His Tyr Trp Arg Leu Asp
    50                  55                  60

Ser Ser Arg Asp Gly Trp His Ser Trp Pro Ile Ala His His
65                  70                  75

<210> SEQ ID NO 16
<211> LENGTH: 71
<212> TYPE: PRT
```

<213> ORGANISM: Sus scrofa

<400> SEQUENCE: 16

Arg Asp Val Arg Asp Tyr Phe Met Ser Cys Pro Gly Arg Gly His Ala
1               5                   10                  15

His Arg Asn Ala Thr His Arg Gly Asp Asp Arg Cys Ser Pro Asp Leu
            20                  25                  30

Val Leu Thr Ala Leu Leu Ser Asp Asn His Gly Ala Thr Tyr Ala Phe
        35                  40                  45

Arg Gly Thr His Tyr Trp Arg Leu Asp Thr Ser Arg Asp Gly Trp His
    50                  55                  60

Ser Trp Pro Ile Asp His Gln
65                  70

<210> SEQ ID NO 17
<211> LENGTH: 78
<212> TYPE: PRT
<213> ORGANISM: Mus musculus

<400> SEQUENCE: 17

Leu Asp Ala Arg Asp Tyr Phe Val Ser Cys Pro Gly Arg Gly His Gly
1               5                   10                  15

Arg Pro Arg Asn Gly Thr Ala His Gly Asn Ser Thr His Pro Met His
            20                  25                  30

Ser Arg Cys Ser Pro Asp Pro Gly Leu Thr Ala Leu Leu Ser Asp His
        35                  40                  45

Arg Gly Ala Thr Tyr Ala Phe Thr Gly Ser His Tyr Trp Arg Leu Asp
    50                  55                  60

Ser Ser Arg Asp Gly Trp His Ser Trp Pro Ile Ala His His
65                  70                  75

<210> SEQ ID NO 18
<211> LENGTH: 398
<212> TYPE: PRT
<213> ORGANISM: Homo sapiens

<400> SEQUENCE: 18

Ile Glu Gln Cys Ser Asp Gly Trp Ser Phe Asp Ala Thr Thr Leu Asp
1               5                   10                  15

Asp Asn Gly Thr Met Leu Phe Phe Lys Asp Glu Phe Val Trp Lys Ser
            20                  25                  30

His Arg Gly Ile Arg Glu Leu Ile Ser Glu Arg Trp Lys Asn Phe Ile
        35                  40                  45

Gly Pro Val Asp Ala Ala Phe Arg His Gly His Thr Ser Val Tyr Leu
    50                  55                  60

Ile Lys Gly Asp Lys Val Trp Val Tyr Thr Ser Pro Lys Ser Leu Gln
65                  70                  75                  80

Asp Glu Phe Pro Gly Ile Pro Phe Pro Leu Asp Ala Ala Val Glu Cys
                85                  90                  95

His Arg Gly Glu Cys Gln Asp Glu Gly Ile Leu Phe Phe Gln Gly Asn
            100                 105                 110

Arg Lys Trp Phe Trp Asp Leu Thr Thr Gly Thr Lys Lys Glu Arg Ser
        115                 120                 125

Trp Pro Ala Val Gly Asn Cys Thr Ser Ala Leu Arg Trp Leu Gly Arg
    130                 135                 140

Tyr Tyr Cys Phe Gln Gly Asn Gln Phe Leu Arg Phe Asn Pro Val Ser
145                 150                 155                 160

Gly Glu Val Pro Pro Gly Tyr Pro Leu Asp Val Arg Asp Tyr Phe Leu
             165                 170                 175

Ser Cys Pro Gly Arg Gly His Arg Ser His Gly His Glu Ser Thr Arg
             180                 185                 190

Cys Asp Pro Asp Leu Val Leu Ser Ala Met Val Ser Asp Asn His Gly
             195                 200                 205

Ala Thr Tyr Val Phe Ser Gly Ser His Tyr Trp Arg Leu Asp Thr Asn
       210                 215                 220

Arg Asp Gly Trp His Ser Trp Pro Ile Ala His Gln Trp Pro Gln Gly
225                 230                 235                 240

Pro Ser Thr Val Asp Ala Ala Phe Ser Trp Glu Asp Lys Leu Tyr Leu
             245                 250                 255

Ile Gln Asp Thr Lys Val Tyr Val Phe Leu Thr Lys Gly Gly Tyr Thr
             260                 265                 270

Leu Val Asn Gly Tyr Pro Lys Arg Leu Glu Lys Glu Leu Gly Ser Pro
       275                 280                 285

Pro Val Ile Ser Leu Glu Ala Val Asp Ala Ala Phe Val Cys Pro Gly
       290                 295                 300

Ser Ser Arg Leu His Ile Met Ala Gly Arg Arg Leu Trp Trp Leu Asp
305                 310                 315                 320

Leu Lys Ser Gly Ala Gln Ala Thr Trp Thr Glu Leu Pro Trp Pro His
             325                 330                 335

Glu Lys Val Asp Gly Ala Leu Cys Met Glu Lys Pro Leu Gly Pro Asn
             340                 345                 350

Ser Cys Ser Thr Ser Gly Pro Asn Leu Tyr Leu Ile His Gly Pro Asn
       355                 360                 365

Leu Tyr Cys Tyr Arg His Val Asp Lys Leu Asn Ala Ala Lys Asn Leu
       370                 375                 380

Pro Gln Pro Gln Arg Val Ser Arg Leu Leu Gly Cys Thr His
385                 390                 395

<210> SEQ ID NO 19
<211> LENGTH: 460
<212> TYPE: PRT
<213> ORGANISM: Oryctolagus cuniculus

<400> SEQUENCE: 19

Met Val Lys Ala Ser Gly Ile Pro Ile Ala Leu Gly Val Trp Gly Leu
1               5                   10                  15

Cys Trp Ser Leu Ala Thr Val Asn Ser Val Pro Leu Thr Ser Ala His
             20                  25                  30

Gly Asn Val Thr Glu Gly Glu Ser Gly Thr Lys Pro Glu Ala Asp Val
         35                  40                  45

Ile Glu Gln Cys Ser Asp Gly Trp Ser Phe Asp Ala Thr Thr Leu Asp
     50                  55                  60

Asp Asn Gly Thr Met Leu Phe Phe Lys Asp Glu Phe Trp Lys Ser
65                  70                  75                  80

His Arg Gly Ile Arg Glu Leu Ile Ser Glu Arg Trp Lys Asn Phe Ile
             85                  90                  95

Gly Pro Val Asp Ala Ala Phe Arg His Gly His Thr Ser Val Tyr Leu
            100                 105                 110

Ile Lys Gly Asp Lys Val Trp Val Tyr Thr Ser Glu Lys Asn Glu Lys
        115                 120                 125

Val Tyr Pro Lys Ser Leu Gln Asp Glu Phe Pro Gly Ile Pro Phe Pro

```
              130                 135                 140
Leu Asp Ala Ala Val Glu Cys His Arg Gly Glu Cys Gln Asp Glu Gly
145                 150                 155                 160

Ile Leu Phe Phe Gln Gly Asn Arg Lys Trp Phe Trp Asp Leu Thr Thr
                165                 170                 175

Gly Thr Lys Lys Glu Arg Ser Trp Pro Ala Val Gly Asn Cys Thr Ser
                180                 185                 190

Ala Leu Arg Trp Leu Gly Arg Tyr Tyr Cys Phe Gln Gly Asn Gln Phe
                195                 200                 205

Leu Arg Phe Asn Pro Val Ser Gly Glu Val Pro Pro Gly Tyr Pro Leu
        210                 215                 220

Asp Val Arg Asp Tyr Phe Leu Ser Cys Pro Gly Arg Gly His Arg Ser
225                 230                 235                 240

Ser His Arg Asn Ser Thr Gln His Gly His Glu Ser Thr Arg Cys Asp
                245                 250                 255

Pro Asp Leu Val Leu Ser Ala Met Val Ser Asp Asn His Gly Ala Thr
                260                 265                 270

Tyr Val Phe Ser Gly Ser His Tyr Trp Arg Leu Asp Thr Asn Arg Asp
        275                 280                 285

Gly Trp His Ser Trp Pro Ile Ala His Gln Trp Pro Gln Gly Pro Ser
        290                 295                 300

Thr Val Asp Ala Ala Phe Ser Trp Glu Asp Lys Leu Tyr Leu Ile Gln
305                 310                 315                 320

Asp Thr Lys Val Tyr Val Phe Leu Thr Lys Gly Gly Tyr Thr Leu Val
                325                 330                 335

Asn Gly Tyr Pro Lys Arg Leu Glu Lys Glu Leu Gly Ser Pro Pro Val
                340                 345                 350

Ile Ser Leu Glu Ala Val Asp Ala Ala Phe Val Cys Pro Gly Ser Ser
        355                 360                 365

Arg Leu His Ile Met Ala Gly Arg Arg Leu Trp Trp Leu Asp Leu Lys
        370                 375                 380

Ser Gly Ala Gln Ala Thr Trp Thr Glu Leu Pro Trp Pro His Glu Lys
385                 390                 395                 400

Val Asp Gly Ala Leu Cys Met Glu Lys Pro Leu Gly Pro Asn Ser Cys
                405                 410                 415

Ser Thr Ser Gly Pro Asn Leu Tyr Leu Ile His Gly Pro Asn Leu Tyr
                420                 425                 430

Cys Tyr Arg His Val Asp Lys Leu Asn Ala Ala Lys Asn Leu Pro Gln
                435                 440                 445

Pro Gln Arg Val Ser Arg Leu Leu Gly Cys Thr His
450                 455                 460
```